US008847004B2

(12) United States Patent
Murphy et al.

(10) Patent No.: US 8,847,004 B2
(45) Date of Patent: Sep. 30, 2014

(54) HUMANIZED M-CSF MICE

(75) Inventors: Andrew J. Murphy, Croton-on-Hudson, NY (US); Sean Stevens, San Francisco, CA (US); Chozhavendan Rathinam, New Haven, CT (US); Elizabeth Eynon, New Haven, CT (US); Markus Manz, Zollikon (CH); Richard Flavell, Guilford, CT (US); George D. Yancopoulos, Yorktown Heights, NY (US)

(73) Assignees: Regeneron Pharmaceuticals, Inc., Tarrytown, NY (US); Yale University, New Haven, CT (US); Institute for Research in Biomedicine (IRB), Bellinzona (CH)

( * ) Notice: Subject to any disclaimer, the term of this patent is extended or adjusted under 35 U.S.C. 154(b) by 0 days.

(21) Appl. No.: 13/372,787

(22) Filed: Feb. 14, 2012

(65) Prior Publication Data

US 2013/0042330 A1 Feb. 14, 2013

Related U.S. Application Data

(60) Provisional application No. 61/442,946, filed on Feb. 15, 2011.

(51) Int. Cl.
*A01K 67/027* (2006.01)
(52) U.S. Cl.
CPC ......... *A01K 67/027* (2013.01); *A01K 2227/105* (2013.01)
USPC .................................. 800/18; 800/9
(58) Field of Classification Search
None
See application file for complete search history.

(56) References Cited

U.S. PATENT DOCUMENTS

| 5,573,930 | A | * | 11/1996 | Ladner et al. ................ 435/69.5 |
| 7,273,753 | B2 | | 9/2007 | Crawford et al. |
| 2003/0028911 | A1 | | 2/2003 | Huang et al. |
| 2008/0311095 | A1 | | 12/2008 | Holmes et al. |

OTHER PUBLICATIONS

Van Der Weyden et al, Tools for Targeted Manipulation of the Mouse Genome. Physiological Genomics, 2002. 11:133-164.*
Chicha et al, Human Adaptive Immune System Rag2-/- γc -/- Mice. Annals of NY Academy of Science, 2005. 1044:236-243.*
Abboud et al., "Analysis of the Mouse CSF-1 Gene Promoter in a Transgenic Mouse Model" The Journal of Histochemistry & Cytochemistry, 51(7):941-949 (2003).
Cheng et al., "Therapeutic Antibodies Targeting CSF1 Impede Macrophage Recruitment in a Xenograft Model of Tenosynovial Giant Cell Tumor" Sarcoma, Article ID 174528, pp. 1-7 (2010).
Dai et al., "Incomplete restoration of colony-stimulating factor 1 (CSF-1) function in CSF-1-deficient Csflop/Csflop mice by transgenic expression of cell surface CSF-1" Blood 103(3):1114-1123 (Feb. 1, 2004).
Irvine et al., "Colony-stimulating factor-1 (CSF-1) delivers a proatherogenic signal to human macrophages" Journal of Leukocyte Biology, 85:278-288 (Feb. 2009).
The Jackson Laboratory, "Strain Name: C; 129S4-Rag2tm1.1Flv; Csf1tm1.1(CSF1)Flv; Il2rgtm1.1Flv/J" JAX Mice Database, http://jaxmic.jax.org/strain/107708.html, 6 pages (Jan. 26, 2012).
Kirma et al., "Overexpression of the Colony-Stimulating Factor (CSF-1) and/or Its Receptor c-fms in Mammary Glands of Transgenic Mice Results in Hyperplasia and Tumor Formulation" Cancer Resesarch, 64:4162-4170 (Jun. 15, 2004).
Pixley et al., "CSF-1 regulation of the wandering macrophage: complexity in action" Trends in Cell Biology, 14 (11):628-638 (Nov. 2004).
Pollard, Jeffrey W. "Tumour-educated macrophages promote tumour progression and metastasis" Nature Reviews, 4:71-78 (Jan. 2004).
Rathinam et al., "Efficient differentiation and function of human macrophages in humaized CSF-1 mice" Blood, 1118 (11):3119-3132 (Sep. 15, 2011).
Rathinam et al., "Efficient differentiation and function of human macrophages in humaized CSF-1 mice" Blood, 1118 (11):3119-3128 (Sep. 15, 2011)—Supplemental Figures.
Rieger et al., "Hematopoietic Cytokines Can Instruct Lineage Choice" Science, 325:217-218 (Jul. 10, 2009).
Ryan et al., "Rescue of the colony-stimulating factor 1 (CSF-1)-nullizygous mouse (Csflop/Csflop) phenotype with CSF-1 transgene and identification of sites of local CSF-1 synthesis" Blood, 98(1):74-84 (Jul. 2001).
Sarrazin et al., "MafB Restricts M-CSF-Dependent Myeloid Commitment Divisions of Hematopoietic Stem Cells" Cell, 138:300-313 (Jul. 24, 2009).
Scudellari, Megan "The innate debate over HSCs" Nature Reports Stem Cells, 1 page, (published online Aug. 6, 2009 / doi: 10.1038/stemcells2009.103).
Stanley, E. Richard, "Lineage Commitment: Cytokines Instruct, At Last!" Cell Stem Cell, 5:234-236 (Sep. 4, 2009).
Wei et al., "Transgenic expression of CSF-1 in CSF-1 receptor-expressing cells lead to macrophage activation, osteoporosis, and early death" Journal of Leukocyte Biology, 80:1445-1453 (Dec. 2006).

(Continued)

*Primary Examiner* — Joseph Woitach
*Assistant Examiner* — Kimberly A Aron
(74) *Attorney, Agent, or Firm* — Tor Smeland; Margarita Zippin; Michael B. Rubin

(57) ABSTRACT

Genetically modified mice comprising a nucleic acid sequence encoding a human M-CSF protein are provided. Also provided are genetically modified mice comprising a nucleic acid sequence encoding a human M-CSF protein that have been engrafted with human cells such as human hematopoietic cells, and methods for making such engrafted mice. These mice find use in a number of applications, such as in modeling human immune disease and pathogen infection; in in vivo screens for agents that modulate hematopoietic cell development and/or activity, e.g. in a healthy or a diseased state; in in vivo screens for agents that are toxic to hematopoietic cells; in in vivo screens for agents that prevent against, mitigate, or reverse the toxic effects of toxic agents on hematopoietic cells; in in vivo screens of human hematopoietic cells from an individual to predict the responsiveness of an individual to a disease therapy, etc.

16 Claims, 22 Drawing Sheets

(56) References Cited

OTHER PUBLICATIONS

Yu et al., "CSF-1 receptor structure/function in MacCsf1r-/- macrophages: regulation of proliferation, differentiation, and morphology" Journal of Leukocyte Biology, 84:852-863 (Sep. 2008).

Chen et al., "Expression of human cytokines dramatically improves reconstitution of specific human-blood lineage cells in humanized mice" PNAS (Dec. 22, 2009) 106(51):21783-21788.

* cited by examiner

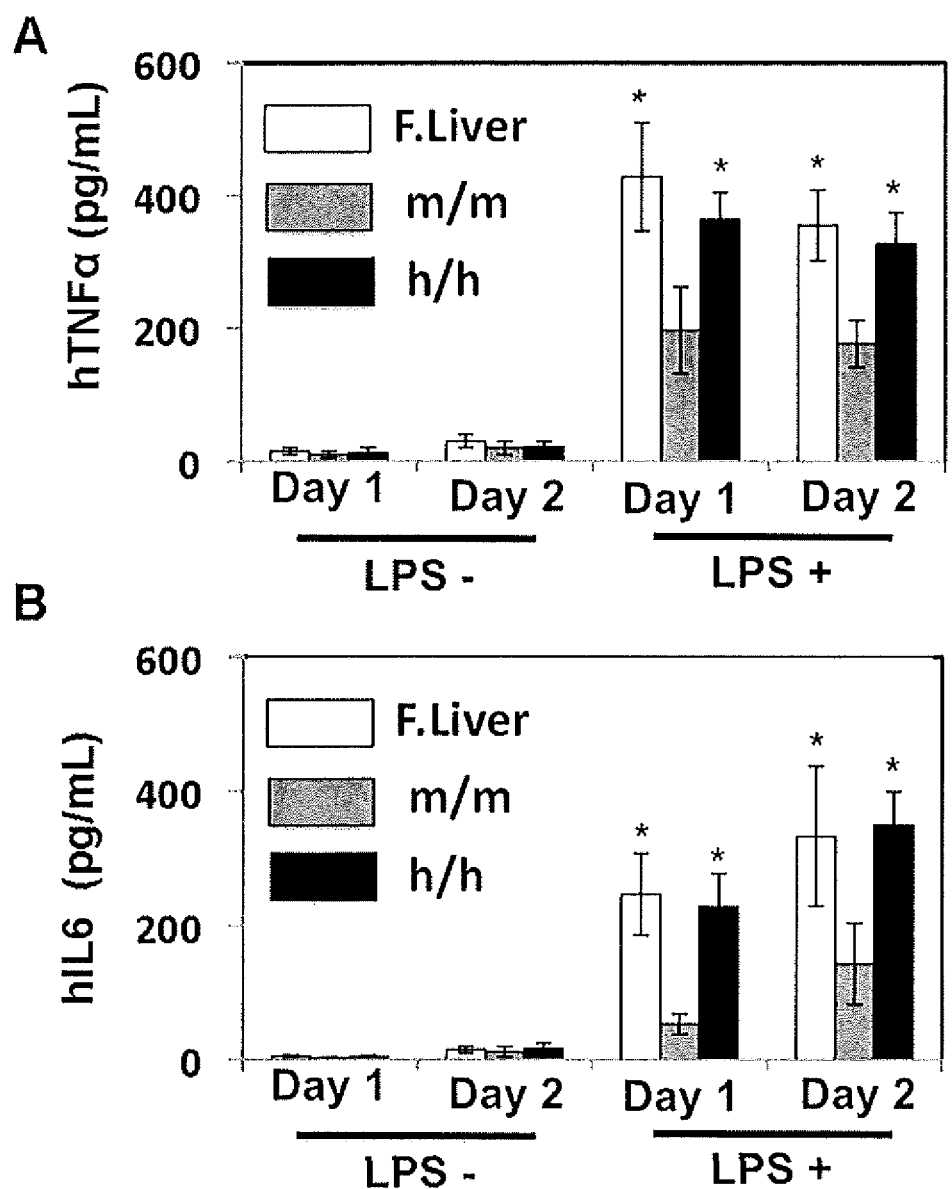
FIG. 7A,B

HUMANIZED M-CSF MICE

CROSS REFERENCE TO RELATED APPLICATIONS

Pursuant to 35 U.S.C. §119 (e), this application claims priority to the filing date of the U.S. Provisional Patent Application Ser. No. 61/442,946 filed Feb. 15, 2011; the disclosure of which is herein incorporated by reference.

FIELD OF INVENTION

The invention relates to genetically modified mice comprising a gene encoding a human M-CSF protein, and mice that comprise further modifications that support engraftment of human hematopoietic cells.

BACKGROUND

The development of animal models to study human diseases has significantly advanced understanding of the underlying mechanisms of several diseases, including cancer. To date, animal models, particularly mice, have proven to be excellent candidates for the evaluation of the efficiency and efficacy of drugs and therapy options. While the utilization of these surrogate models to study human biology and diseases can be largely justified (due to ethical and technical constrains on the conduct of experimental therapies in humans) studies have highlighted potential limitations of extrapolating data from mice to humans (Mestas J, Hughes C C. (2004) Of mice and not men: differences between mouse and human immunology. J. Immunol. 172:2731-2738).

To overcome these issues, there has been a long-standing interest in developing humanized mouse models. Intensive work by several groups have successfully demonstrated the feasibility of studying human biology and diseases in mice. Since having a functional and effective immune system in recipients will result in the elimination of the transplanted tissues/cells of human origin, using genetic mutants that lack cells of the adaptive immune system such as T, B and NK cells has significantly contributed to the success of the humanized mouse model. Accordingly, the most effective candidates of humanized mouse models include the NOD-SCID and the Balb/c strains that lack genes including recombination activating genes (RAG), common gamma chain (γC, also known as "interleukin 2 receptor, gamma", or IL2rg), beta2 microglobin (B2M) and Perforin 1 (Prf1) (Shultz L D, et al. (2007) Humanized mice in translational biomedical research, Nat. Rev. Immunol. 7:118-130). Several studies over the past few decades have demonstrated the feasibility of transplanting several types of human tissues, including peripheral blood leukocytes, fetal liver cells, fetal bone, fetal thymus, fetal lymph nodes, vascularized skin, artery segments and either mobilized or cord blood hematopoietic stem cells (HSCs), into certain humanized mice (Macchiarini F., et al. (2005) Humanized mice: are we there yet? J. Exp. Med. 202:1307-1311). This approach is thought to provide better model systems since the data obtained from human cells in these mice might reflect the physiology of the human system. A major avenue of investigation in the field is to generate mice with a complete hematopoietic system and a functional immune system of the human origin. While significant progress has been made in generating immunocompromised mice with human T lymphocytes, B lymphocytes, NK cells and dendritic cells (DCs), there are still several challenges in the field, one of which is poor myeloid differentiation in the humanized mice.

Interestingly, there has been much progress in generating human T cells, B cells, NK cells and dendritic cells (DCs) from hematopoietic stem cells (HSCs) in humanized mice. In addition to the individual hematopoietic compartment, injection of human HSCs in these mice resulted in the reconstitution of lymphoid organs such as thymus and spleen. Nevertheless, the frequencies of myeloid cells, particularly granulocytes, macrophages, erythrocytes and megakaryocytes, are very low—a result that is probably due to inefficient myelopoiesis from human HSCs in these mice (Shultz et al. (2007); Macchiarini et al. (2005)). In view of the fact that the cells of myeloid origin (such as erythrocytes and megakaryocytes) are vital for the normal functioning of the blood system, and granulocytes and macrophages are critical for the development of the adaptive immune system, generating humanized mice with an efficient human myelopoiesis is of paramount importance.

Accordingly, there is a need in the art for genetically modified mice that are capable of improved human myelopoiesis upon engraftment with human HSCs (Manz M G. Human-hemato-lymphoid-system mice: opportunities and challenges. Immunity. 2007 May; 26(5):537-41).

SUMMARY

Genetically modified mice comprising a nucleic acid sequence encoding a human M-CSF protein are provided. Also provided are genetically modified mice comprising a nucleic acid sequence encoding a human M-CSF protein that have been engrafted with human cells such as human hematopoietic cells, and methods for making such engrafted mice. These mice find use in a number of applications, such as in modeling human immune disease and pathogen infection; in in vivo screens for agents that modulate hematopoietic cell development and/or activity, e.g. in a healthy or a diseased state; in in vivo screens for agents that are toxic to hematopoietic cells; in in vivo screens for agents that prevent against, mitigate, or reverse the toxic effects of toxic agents on hematopoietic cells; in in vivo screens of human hematopoietic cells from an individual to predict the responsiveness of an individual to a disease therapy, etc.

In some aspects of the invention, a humanized M-CSF mouse is provided, where the humanized M-CSF comprises a nucleic acid sequence that encodes a human M-CSF protein and is operably linked to regulatory sequence 5' of the mouse M-CSF structural gene locus, e.g. the mouse M-CSF promoter, 5'UTR, etc. In some embodiments the mouse comprises two copies of the nucleic acid sequence. In some embodiments, the nucleic acid sequence is located in the mouse genome within the mouse M-CSF locus. In some embodiments, the nucleic acid sequence is operably linked to the endogenous mouse M-CSF promoter at the mouse M-CSF locus, i.e. the mouse is a M-CSF$^{h/m}$ mouse. In some embodiments, the mouse comprises two alleles in which the nucleic acid sequence is located in the mouse genome within the mouse M-CSF locus. In some embodiments, the nucleic acid sequence of both alleles is operably linked to the endogenous mouse M-CSF promoter at the mouse M-CSF locus, i.e. the mouse is a M-CSF$^{h/h}$ mouse. In some embodiments, the humanized M-CSF mouse comprises a null mutation in at least one mouse M-CSF allele. In some embodiments, the humanized M-CSF mouse comprises a null mutation in both mouse M-CSF alleles. In some such embodiments, the null mutation is a deletion of mouse M-CSF exons 2-9.

In some embodiments, the mouse expresses human M-CSF in bone marrow, spleen, blood, liver, brain, lung, testis, and kidney. In some embodiments, the amount of human M-CSF expressed is substantially the same as the amount of mouse M-CSF expressed in a wild-type mouse. In some embodiments, bone marrow mesenchymal stromal cells of the humanized M-CSF mouse express an amount of human M-CSF that is substantially the same as the amount of mouse M-CSF expressed by wild-type mouse bone marrow mesenchymal stromal cells. In some embodiments, the humanized M-CSF mouse exhibits a physiological concentration of M-CSF in blood and/or tissue. In some embodiments, the mouse expresses both mouse M-CSF and human M-CSF. In other embodiments, the only M-CSF expressed by the mouse is human M-CSF.

In some embodiments, the mouse secretes sufficient human M-CSF to differentiate engrafted human hematopoietic stem cells into human monocytes, human macrophages, and human osteoclasts. In some embodiments, the mouse secretes an effective amount of M-CSF to stimulate the development of human macrophages from human monocytes that result from an engraftment of human hematopoietic stem cells into the mouse. In some embodiments, the mouse secretes an effective amount of M-CSF to stimulate the development of a human hematopoietic stem cell into a monoblast, a monoblast into a human promonocyte, a human promonocyte into a human monocyte, and a human monocyte into a human macrophage, in a mouse engrafted with human hematopoietic stem cells. In some embodiments, the effective amount of human M-CSF secreted in the mouse is substantially the same amount of mouse M-CSF secreted by a wild-type mouse to achieve a corresponding result (e.g., an effective amount of mouse M-CSF to stimulate development of a mouse macrophage from a mouse monocyte).

In some embodiments, the transcriptional and translational control of human M-CSF in the genetically modified mouse is identical or substantially identical to the transcriptional and translational control of mouse M-CSF in a mouse that lacks a modification of its endogenous mouse M-CSF gene.

In some embodiments, the physiological concentration of human M-CSF in the humanized M-CSF mouse results from secretion of human M-CSF from the same cell types that secrete mouse M-CSF in a wild-type mouse that has a mouse M-CSF gene and that lacks a nucleic acid encoding a human M-CSF protein. In other words, one or more M-CSF isoforms are expressed in a normal tissue-specific and developmental pattern.

In some embodiments, the mouse expresses a human M-CSF isoform selected from proteoglycan M-CSF, glycoprotein M-CSF, and cell surface M-CSF, and a combination thereof. In one embodiment, the mouse expresses at least two of the isoforms in a normal tissue-specific and developmental pattern. In a specific embodiment, the mouse expresses human proteoglycan CSF-1 and human glycoprotein M-CSF and human cell surface M-CSF.

In some embodiments, the mouse comprises human macrophages that are not thymic T cell-derived macrophages. In some embodiments, the mouse comprises human macrophages that exhibit M-CSF-dependent podosome formation stimulated by human M-CSF expressed in the mouse.

In some embodiments, the mouse is homozygous null for Rag2. In some embodiments, the mouse is homozygous null for IL2rg. In some embodiments, the mouse is homozygous null for Rag2 and for IL2rg. In some embodiments, the mouse comprises human cells. In some embodiments, the human cells are hematopoietic cells.

In some aspects of the invention, a mouse model of the human immune system is provided, the mouse model comprising 2 null alleles for Rag2, 2 null alleles for IL2rg, a nucleic acid sequence that encodes a human M-CSF protein operably linked to the promoter of the mouse M-CSF gene, and human hematopoietic cells. In other words, the mouse is an engrafted $Rag2^{-/-}$ $IL2rg^{-/-}$ hM-CSF mouse, where hM-CSF denotes that the mouse comprises at least one nucleic acid encoding a human M-CSF gene. In some embodiments, the engrafted $Rag2^{-/-}$ $IL2rg^{-/-}$ hM-CSF mouse is a BALB/c strain mouse comprising these genetic modifications. In some embodiments, the mouse comprises other genetic modifications as well.

In some embodiments, the engrafted $Rag2^{-/-}$ $IL2rg^{-/-}$ hM-CSF mouse at about 12 weeks of age exhibits an increased frequency of human $CD14^+CD33^+$ ($hCD14^+CD33^+$) cells in bone marrow, spleen, and peripheral blood as compared with a mouse comprising human hematopoietic cells that expresses mouse M-CSF but not human M-CSF. In a specific embodiment, the increase in $hCD14^+CD33^+$ cells of bone marrow over a mouse expressing only mouse M-CSF is about 5 to about 15 fold, in one embodiment about 12- to about 14-fold. In a specific embodiment, the increase in $hCD14^+CD33^+$ cells of spleen over a mouse comprising human hematopoietic cells that expresses only mouse M-CSF is about 2- to about 6-fold, in one embodiment about 5- to about 6-fold. In a specific embodiment, the increase in $hCD14^+CD33^+$ cells of peripheral blood over a mouse comprising human hematopoietic cells that expresses only mouse M-CSF is about 2- to about 8-fold, in one embodiment about 5- to about 7-fold.

In some embodiments, the engrafted $Rag2^{-/-}$ $IL2^{-/-}$ hM-CSF mouse at about 12 weeks of age exhibits a level of $hCD14^+CD33^+$ monocyte/macrophage lineage cells in blood of about 15 to about 40%, in one embodiment about 30%. In one embodiment, the genetically modified engrafted mouse at about 16 weeks of age exhibits a level of $hCD14^+CD33^+$ monocyte/macrophage lineage cells in blood of about 15 to about 30%, in one embodiment about 22%. In one embodiment, the genetically modified engrafted mouse at about 20 weeks of age exhibits a level of $hCD14^+CD33^+$ monocyte/macrophage lineage cells in blood of about 5 to about 15%, in one embodiment about 10%. In one embodiment, the genetically modified engrafted mouse at about 20 weeks of age exhibits a level of $hCD14^+CD33^+$ monocyte/macrophage lineage cells in blood that is about 4- to 8-fold higher than the level in an engrafted mouse that expresses mouse M-CSF but not human M-CSF, in one embodiment about 6-fold higher.

In some embodiments, the engrafted $Rag2^{-/-}$ $IL24^{-/-}$ hM-CSF mouse at about 12 weeks of age exhibits a level of $hCD14^+CD33^+CD45^+$ cells in liver that is about 1.5- to about 6-fold higher than an engrafted mouse that expresses mouse M-CSF but not human M-CSF. In one embodiment, the genetically modified engrafted mouse at about 12 weeks of age exhibits a level of $hCD14^+CD33^+CD45^+$ cells in lung that is about 1.5- to about 10-fold higher than an engrafted mouse that expresses mouse M-CSF but not human M-CSF. In one embodiment, the genetically modified engrafted mouse at about 12 weeks of age exhibits a level of human $hCD14^+CD33^+CD45^+$ cells in peritoneum or in skin that is about 2- to about 3-fold higher than an engrafted mouse that expresses mouse M-CSF but not human M-CSF.

In some embodiments, the engrafted $Rag2^{-/-}$ $IL2rg^{-/-}$ hM-CSF mouse exhibits a response to LPS injection that is about 1.5- to about 6-fold greater with respect to percentage of $hCD14^+CD33^+$ cells in liver than mice that lack a human M-CSF, in one embodiment about 2- to about 4-fold; in lung the LPS response with respect to $hCD14^+CD33^+$ cells is about 1.5- to 10-fold, in one embodiment about 2- to 3-fold; in skin the LPS response with respect to $hCD14^+CD33^+$ is about 2- to about 5-fold, in one embodiment about 3- to about 4-fold; in peritoneum the LPS response with respect to hCD14$^+$CD33$^+$ is about 2- to about 5-fold, in one embodiment about 3- to about 4-fold.

In some embodiments, the engrafted Rag2$^{-/-}$ IL2$^{-/-}$ hM-CSF mouse exhibits in response to LPS stimulation an enhanced pro-inflammatory cytokine response, wherein the enhancement over a genetically modified and engrafted mouse that lacks a hM-CSF gene is about 2- to at least about 5-fold with respect to the level of activation and/or differentiation of a cell type that is responsive to the pro-inflammatory cytokine.

In some embodiments, the engrafted Rag2$^{-/-}$ IL2$^{-/-}$ hM-CSF mouse exhibits an enhanced production of hCD14$^+$CD33$^+$hCD45$^+$ cells in spleen about 48 hours following LPS injection, wherein the enhancement is about 2- to about 5-fold, in one embodiment 4- to about 5-fold, over an engrafted mouse that expresses mouse M-CSF but not human M-CSF.

In some embodiments, the engrafted Rag2$^{-/-}$ IL2rg$^{-/-}$ hM-CSF mouse exhibits an enhanced production of serum human IL-6 in response to LPS, wherein the level of hIL-6 about 6 hours after LPS injection is enhanced about 2- to about 5-fold over an engrafted mouse that expresses mouse M-CSF but not human M-CSF, in one embodiment about 3- to about 4-fold.

In some embodiments, the engrafted Rag2$^{-/-}$ IL2$^{-/-}$ hM-CSF mouse exhibits en enhanced production of serum human TNFα in response to LPS, wherein the level of hTNFα about 6 hours after LPS injection is enhanced about 2- to about 4-fold over an engrafted mouse that expresses mouse M-CSF but not human M-CSF, in one embodiment about 2- to about 3-fold.

In some embodiments, a monocyte and/or macrophage isolated from the engrafted Rag2$^{-/-}$ IL2rg$^{-/-}$ hM-CSF mouse exhibits in vitro secretion upon LPS stimulation that is about 2- to 3-fold higher with respect to hTNFα than an engrafted mouse that expresses mouse M-CSF but not human M-CSF.

In some embodiments, a monocyte and/or macrophage isolated from the engrafted Rag2$^{-/-}$ IL2rg$^{-/-}$ hM-CSF mouse exhibits in vitro secretion upon LPS stimulation that is about 2- to 4-fold higher with respect to hIL-6 than an engrafted mouse that expresses mouse M-CSF but not human M-CSF.

In some embodiments, a monocyte and/or macrophage isolated from the engrafted Rag2$^{-/-}$ IL2rg$^{-/-}$ hM-CSF mouse exhibits in vitro secretion upon poly I:C stimulation that is about 3- to 6-fold higher with respect to hIFNα than an engrafted mouse that expresses mouse M-CSF but not human M-CSF.

In some embodiments, a monocyte and/or macrophage isolated from the engrafted Rag2$^{-/-}$ IL2rg$^{-/-}$ hM-CSF mouse exhibits in vitro secretion upon poly I:C stimulation that is about 2- to 3-fold higher with respect to hIFNβ than an engrafted mouse that expresses mouse M-CSF but not human M-CSF.

In some embodiments, a human monocyte and/or macrophage isolated from the engrafted Rag2$^{-/-}$ IL2$^{-/-}$ hM-CSF mouse exhibits enhanced phagocytosis as compared with an engrafted mouse that expresses mouse M-CSF but not human M-CSF. In one embodiment, the enhancement is about double the rate of phagocytosis, as measured by incorporation of labeled bacteria at 37° C. over a 60-minute time period, as compared with human cells from an engrafted mouse that expresses mouse M-CSF but not human M-CSF. In one embodiment, the phagocytosis rate as measured above is two fold or more the rate of human cells from an engrafted mouse that expresses mouse M-CSF but not human M-CSF, e.g. 2-fold, 3-fold, or 4-fold or more.

In some embodiments, a human monocyte and/or macrophage isolated from the engrafted Rag2$^{-/-}$ IL2$^{-/-}$ hM-CSF mouse exhibits enhanced chemotaxis in vitro in response to Mip3β as compared with an engrafted mouse that expresses mouse M-CSF but not human M-CSF. In one embodiment, the enhancement is about 1.5-fold to 3-fold or more, e.g. about 1.5-fold, 2-fold, 3-fold, 4-fold or more, as measured by number of migrated cells at 30 or 60 minutes following Mip3β exposure, as compared with a human monocyte and/or macrophage from a engrafted mouse that expresses mouse M-CSF but not human M-CSF.

In some embodiments, a human monocyte and/or macrophage isolated from the engrafted Rag2$^{-/-}$ IL2$^{-/-}$ M-CSF$^h$ mouse exhibits in vitro secretion upon poly I:C stimulation that is about 3- to 6-fold higher with respect to hIFNα than an engrafted mouse that expresses mouse M-CSF but not human M-CSF.

In some embodiments, a human monocyte and/or macrophage isolated from the engrafted Rag2$^{-/-}$ IL2rg$^{-/-}$ hM-CSF mouse exhibits upregulation in vitro of a co-stimulatory molecule in response to LPS stimulation. In one embodiment, the co-stimulatory molecule is selected from human CD40, human CD80, human CD86, human HLA-DR, and a combination thereof.

In some aspects of the invention, a genetically modified engrafted mouse is provided, wherein the mouse comprises an engraftment of human hematopoietic cells, is Rag2$^{-/-}$ Il2rg$^{-/-}$, comprises a null allele for mouse M-CSF, and comprises a nucleic acid sequence encoding a human M-CSF at the endogenous M-CSF locus, wherein the mouse exhibits an enhancement, or increased number, of human myeloid cells as compared with that expresses mouse M-CSF but not human M-CSF.

In some embodiments, the enhancement comprises at least a doubling in the number of hCD14$^+$CD33$^+$ cells in a portion of the mouse selected from bone marrow, spleen, and peripheral blood. In a specific embodiment, the enhancement comprises a tripling of the hCD14$^+$CD33$^+$ cells. In another embodiment, the enhancement comprises a 4- to 5-fold increase or more in the number of hCD14$^+$CD33$^+$ cells.

In some embodiments, the enhancement comprises a 2- to 3-fold increase in the number of hCD14$^+$CD33$^+$hCD45$^+$ cells in a compartment of the mouse selected from skin and peritoneum.

In some embodiments, the enhancement comprises a 1.5- to 10-fold increase in the number of hCD14$^+$CD33$^+$hCD45$^+$ cells in a compartment of the mouse selected from liver and lung.

In some embodiments, the enhancement comprises a 4- to 5-fold increase in the number of hCD14$^+$CD33$^+$hCD45$^+$ spleen cells at about 48 hours post-LPS stimulation.

In some embodiments, the enhancement comprises a 2- to 4-fold increase in LPS-stimulated serum hIL-6 or LPS-stimulated serum hTNFα.

In some embodiments, the enhancement comprises a 2- to 3-fold increase in human MIP3β-stimulated in vitro migration of hCD14$^+$CD33$^+$ cells.

In some aspects of the invention, a mouse model for a human pathogen is provided, the mouse model comprising 2 null alleles for Rag2, 2 null alleles for IL2rg, a nucleic acid sequence that encodes a human M-CSF protein operably linked to the promoter of the mouse M-CSF gene, human hematopoietic cells, and an infection by a human pathogen. In other words, the mouse is an engrafted Rag2$^{-/-}$ IL2$^{-/-}$ hM-CSF mouse that has been infected with a human pathogen. In some embodiments, the pathogen is a virus, a fungus, or a bacterium. In some embodiments, the virus is a human or porcine or avian influenza virus. In some embodiments, the bacterium is a mycobacterium, e.g. *Mycobacterium tuberculosis* (*M. tuberculosis*). In some embodiments, the bacterium is an enterobacterium, e.g. *Salmonella typhi* (*S. typhi*).

In some aspects of the invention, a pluripotent, induced pluripotent, or totipotent mouse cell is provided, comprising a nucleic acid sequence encoding a human M-CSF protein operably linked to the promoter of the mouse M-CSF gene. In one embodiment, the mouse cell is a mouse ES cell.

In some aspects of the invention, a mouse embryo is provided, comprising a nucleic acid sequence encoding a human M-CSF protein operably linked to the promoter of the mouse M-CSF gene.

In some aspects of the invention, a targeting construct for targeting a mouse M-CSF gene is provided, comprising (a) upstream and downstream targeting arms that are complementary or substantially complementary to upstream and downstream nucleotide sequences of either (i) a nucleotide sequence encoding a mouse M-CSF protein, or, (ii) a nucleotide sequence complementary to a nucleotide sequence encoding a mouse M-CSF protein; (b) human nucleic acid sequence encoding a human M-CSF protein or fragment thereof, or a nucleotide sequence encoding the complement of a human M-CSF protein or fragment thereof; and, (c) a marker and/or a selection cassette.

In some aspects of the invention, a human immune cell from a mouse as described herein is provided. In one embodiment, the human immune cell is selected from a human monocyte and a human macrophage. In one embodiment, the human immune cell is selected from a human NK cell, a human B cell, and a human T cell.

In some aspects of the invention, an antibody encoded by a human nucleotide sequence from a mouse as described herein is provided. In one embodiment, the antibody is selected from an IgA, IgD, IgE, IgM, or IgG isotype antibody.

In some aspects of the invention, a nucleotide sequence encoding a human immunoglobulin sequence is provided, wherein the nucleotide sequence is obtained from an engrafted humanized M-CSF mouse according to the invention. In one embodiment, the nucleotides sequence encodes a human variable region of a human immunoglobulin gene or a fragment thereof. In one embodiment, the nucleotide sequence encodes a human TCR variable region or fragment thereof.

In some aspects of the invention, a method for making a humanized M-CSF mouse expressing biologically active human M-CSF is provided. In some embodiments, the method comprises contacting a mouse pluripotent stem cell, e.g. an ES cell or an iPS cell, with a nucleic acid sequence comprising coding sequence for a human M-CSF protein or a ragment thereof and culturing the pluripotent stem cell under conditions that promote the integration of the nucleic acid sequence into the mouse genome; making a mouse from the mouse ES cell that comprises the nucleic acid sequence encoding a human M-CSF protein; and maintaining the mouse under conditions sufficient for the mouse to express human M-CSF from the human M-CSF gene. In some embodiments, the nucleic acid sequence is integrated randomly into the genome. In other embodiments, the nucleic acid sequence is integrated into a target locus. In some such embodiments, the target locus is the endogenous mouse M-CSF locus, e.g. the nucleic acid sequence comprising coding sequence for a human M-CSF protein is flanked by sequences that are homologous to the endogenous mouse M-CSF locus, and the nucleic acid sequence is integrated into the endogenous mouse M-CSF locus by homologous recombination. In some embodiments, the mouse is homozygous null for Rag2. In some embodiments, the mouse is homozygous null for IL2rg. In some embodiments, the mouse is homozygous null for Rag2 and IL2rg, i.e., it is $Rag2^{-/-}$ $IL2rg^{-/-}$.

In some aspects of the invention, a method for making a humanized M-CSF mouse comprising a human hematopoietic system is provided. In some embodiments, the method comprises transplanting into a humanized M-CSF mouse, e.g. a $Rag2^{-/-}$ $IL2rg^{-/-}$ hM-CSF mouse or a sublethally irradiated hM-CSF mouse, a population of cells comprising human hematopoietic progenitor cells. In some embodiments, the human hematopoietic progenitor cells are $CD34_+$ cells. In some embodiments, the human hematopoietic progenitor cells are $CD133_+$. In some embodiments, the human hematopoietic progenitor cells pluripotent stem cells, e.g. ES cells or iPS cells. In some embodiments, the source of the population of cells comprising human hematopoietic progenitor cells is fetal liver. In some embodiments, the source of the cells is bone marrow. In some embodiments, the source of the cells is peripheral blood. In some embodiments, the source of the cells is an in vitro population of cells.

In some aspects of the invention, a method for making a mouse that is infected with a human pathogen is provided. In some embodiments, the method comprises exposing a humanized M-CSF comprising human hematopoietic cells, e.g. an engrafted $Rag2^{-/-}$ $IL2rg^{-/-}$ hM-CSF mouse or an engrafted sublethally irradiated mouse, to a human pathogen, and maintaining the mouse under conditions sufficient for the human pathogen to infect the mouse. In some embodiments, the human pathogen is a human pathogen that does not infect a mouse that lacks one or more of the genetic modifications described herein. In some embodiments, the human pathogen is a human pathogen that is not pathogenic in a mouse that lacks one or more of the genetic modifications described herein.

In some aspects of the invention, a method for making biologically active human M-CSF in a mouse is provided, the method comprising making a humanized M-CSF mouse expressing biologically active human M-CSF as described above and elsewhere herein. In some embodiments, the method comprises purifying biologically active human M-CSF from blood, e.g. serum, or tissue of the mouse. In some embodiments, the method comprises obtaining a cell that expresses biologically active human M-CSF from the mouse, culturing the cell under conditions sufficient for the cell to express and secrete biologically active human M-CSF, and isolating the secreted biologically active human M-CSF. It being noted that in this aspect of the invention the mouse is not required to have any other genetic modifications and that the mouse is useful in making preparations of certain human immune cells. As such, in some aspects of the invention, isolated biologically active human M-CSF obtained from a transgenic mouse is provided.

In some aspects of the invention, a method for making an activated human monocyte or activated human macrophage in a mouse is provided, comprising exposing a humanized M-CSF mouse engrafted with human hematopoietic cells to an immune stimulant, allowing human monocytes or macrophages in the mouse to become activated, and isolating from the mouse human monocytes or human macrophages, wherein the fraction of activated monocytes or activated macrophages are about two-fold to five-fold higher than obtained from an engrafted mouse that is not a humanized M-CSF mouse, i.e. that lacks a human M-CSF gene. In some embodiments, the immune stimulant is an endotoxin. In a specific embodiment, the endotoxin is LPS.

In some aspects of the invention, a method of screening a candidate agent for activity in modulating human hematopoietic cell function is provided. In some embodiments, the method comprises contacting a humanized M-CSF mouse engrafted with human hematopoietic cells, e.g. an engrafted Rag2$^{-/-}$ IL2rg$^{-/-}$ hM-CSF mouse or an engrafted sublethally irradiated hM-CSF mouse, with a candidate agent; and comparing the function of the hematopoietic cells in the mouse model contacted with the candidate agent to the function of the hematopoietic cells in the mouse model that was not contacted with the candidate agent; wherein a modulation in the function of the hematopoietic cells in the mouse contacted with the candidate agent indicates that the candidate agent modulates hematopoietic cell function.

In some aspects of the invention, a method for determining the effect of an agent on a human pathogen is provided, comprising exposing an engrafted humanized M-CSF mouse, e.g. an engrafted Rag2$^{-/-}$ IL2rg$^{-/-}$ hM-CSF mouse or an engrafted sublethally irradiated hM-CSF mouse, to an effective amount of a human pathogen, the effective amount of a pathogen being the amount of pathogen required to produce an infection in the mouse; allowing the pathogen to infect the mouse; measuring a parameter of the infection over time in the presence of the agent; and comparing that measurement to the measurement from an engrafted humanized M-CSF mouse not exposed to the agent. In some embodiments, the agent is provided prior to exposing the mouse to the human pathogen, e.g. to determine the protective effect. In some embodiments, the agent is provided concurrently with exposing the mouse to the human pathogen, e.g. to determine the protective or therapeutic effect. In some embodiments, the agent is provided after exposing the mouse to the human pathogen, e.g. to determine the therapeutic effect. In some embodiments, the mouse upon exposure to a human pathogen mounts a cellular and/or humoral immune response that models infection of a human exposed to the pathogen. In some embodiments, the human pathogen is a pathogen that does not infect a mouse that lacks one or more of the genetic modifications described herein. In some embodiments the human pathogen is a pathogen that infects a wild-type mouse, wherein the wild-type mouse following infection does not model an immune response that a human mounts in response to the pathogen. In some embodiments, the virus is a human or porcine or avian influenza virus. In some embodiments, the bacterium is a mycobacterium, e.g. *Mycobacterium tuberculosis* (*M. tuberculosis*). In some embodiments, the bacterium is an enterobacterium, e.g. *Salmonella typhi* (*S. typhi*). In some embodiments, the mouse is exposed to a known number of infectious units of the human pathogen, and the parameter of infection is the number of infectious units of the human pathogen in a fluid or tissue of the mouse. In some embodiments, the parameter of the infection is a titer in a body fluid of the mouse. In some embodiments, the parameter of the infection is the formulation of a granuloma. In some such embodiments, the granuloma is a lung granuloma. In some such embodiments, the granuloma is a well-defined granuloma.

In some aspects of the invention, a method for determining the effect of an agent on a human pathogen is provided, comprising exposing an engrafted humanized M-CSF mouse, e.g. an engrafted Rag2$^{-/-}$ IL2rg$^{-/-}$ hM-CSF mouse or an engrafted sublethally irradiated hM-CSF mouse, to an effective amount of an antigen of a human pathogen, the effective amount of antigen being the amount of antigen required to promote a cellular and/or humoral response in the mouse; allowing a cellular and/or humoral response to develop; measuring a parameter of the cellular and/or humoral response over time in the presence of the agent; and comparing that measurement to the measurement from an engrafted humanized M-CSF mouse not exposed to the agent. In some embodiments, the agent is provided before exposing the mouse to the antigen from the human pathogen, e.g. to determine the protective effect of the agent. In some embodiments, the agent is provided concurrently with exposing the mouse to the antigen from the human pathogen, e.g. to determine the protective or therapeutic effect of the agent. In some embodiments, the agent is provided after exposing the mouse to antigen from the human pathogen, e.g. to determine the therapeutic effect of the agent. In some embodiments, the mouse upon exposure to a human pathogen mounts a cellular and/or humoral immune response that models infection of a human exposed to the pathogen.

In some embodiments, the antigen is from a human pathogen that does not infect a mouse that lacks one or more of the genetic modifications described herein. In other embodiments the antigen is from a human pathogen that infects a wild-type mouse, wherein the wild-type mouse following infection does not model an immune response that a human mounts in response to the pathogen. In some embodiments, the pathogen is a virus, a fungus, or a bacterium. In some embodiments, the virus is a human or porcine or avian influenza virus. In some embodiments, the bacterium is a mycobacterium, e.g. *Mycobacterium tuberculosis* (*M. tuberculosis*). In some embodiments, the bacterium is an enterobacterium, e.g. *Salmonella typhi* (*S. typhi*).

In some aspects of the invention, a method of screening a candidate agent for toxicity to human hematopoietic cells is provided. In some embodiments, the method comprises contacting a humanized M-CSF mouse engrafted with human hematopoietic cells, e.g. an engrafted Rag2$^{-/-}$ IL2rg$^{-/-}$ hM-CSF mouse, with a candidate agent; and comparing the viability and/or function of the hematopoietic cells in the mouse contacted with the candidate agent to the viability and/or function of the hematopoietic cells in a humanized M-CSF mouse engrafted with human hematopoietic cells that was not contacted with the candidate agent; wherein a decrease in the viability and/or function of the hematopoietic cells in the mouse contacted with the candidate agent indicates that the candidate agent is toxic to the hematopoietic cells.

In some aspects of the invention, a method of screening a candidate agent for the ability to protect human hematopoietic cells from a toxic agent, mitigate the effects of a toxic agent on human hematopoietic cells, or reverse the effects of a toxic agent on human hematopoietic cells is provided. In some embodiments, the method comprises contacting a humanized M-CSF mouse engrafted with human hematopoietic cells, e.g. an engrafted Rag2$^{-/-}$ IL2rg$^{-/-}$ hM-CSF mouse or an engrafted sublethally irradiated hM-CSF mouse, with a toxic agent; contacting the mouse with a candidate agent; and comparing the viability and/or function of the hematopoietic cells in the mouse contacted with the candidate agent to the viability and/or function of hematopoietic cells in a humanized M-CSF mouse engrafted with human hematopoietic cells that were not contacted with the candidate agent; wherein an enhancement in viability and/or function of hematopoietic cells in the mouse model contacted with the candidate agent indicates that the candidate agent protects hematopoietic cells from the toxic agent.

In some aspects of the invention, a method for predicting responsiveness of an individual to treatment with a therapeutic agent is provided. In some embodiments, the method comprises contacting a humanized M-CSF mouse engrafted with human hematopoietic cells from the individual, e.g. an engrafted Rag2$^{-/-}$ IL2rg$^{-/-}$ hM-CSF mouse or an engrafted sublethally irradiated hM-CSF mouse, with a therapeutic agent; and comparing the viability and/or function of the hematopoietic cells in the mouse model contacted with the candidate agent to the viability and/or function of the hematopoietic cells in a humanized M-CSF mouse engrafted with human hematopoietic cells that was not contacted with the candidate agent; wherein a modulation in the viability and/or function of the hematopoietic cells in the mouse contacted with the candidate agent indicates that the individual will have a response to treatment with the therapeutic agent.

BRIEF DESCRIPTION OF THE FIGURES

FIGS. 7A (for hTNFα) and 7B (for h IL-6) illustrate the ability of monocytes/macrophages to secrete pro-inflammatory cytokines in vitro following LPS stimulation. Human CD45$^+$CD14$^+$CD33$^+$ cells from the spleens of human CD34$^+$ cells-engrafted M-CSF$^{m/m}$ and M-CSF$^{h/h}$ mice were isolated after 12 weeks of transplantation; human CD45$^+$CD14$^+$CD33$^+$ cells obtained from the fetal liver served as controls; cells were stimulated in vitro with LPS either for 24 or 48 hours, cell culture supernatants were collected, and levels of human TNFα (A) and IL-6 (B) were quantified through ELISA; mean values of triplicate samples are shown; error bars indicate ±SEM.

DETAILED DESCRIPTION

Figure 1A:
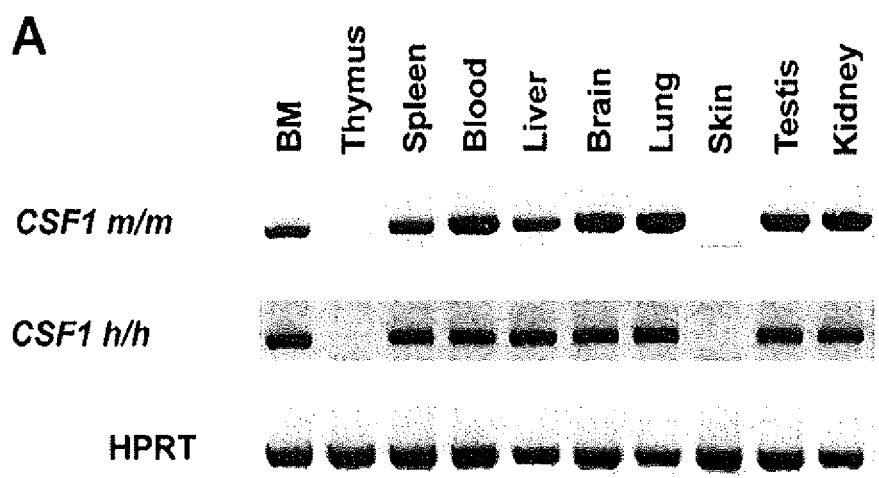
FIG. 1 illustrates, for bone marrow mesenchymal stromal cells, (A) expression of M-CSF; indicated organs from M-CSF$^{m/m}$ and M-CSF$^{h/h}$ were isolated, RNA was extracted and reverse transcription (RT)-PCR analysis was performed either using mouse M-CSF (top) or human M-CSF (middle) specific primers; HPRT level (bottom) was used as control for the input cDNA; data are representative of 2 independent experiments. (B) Indicated organs from M-CSF$^{h/m}$ were isolated, RNA was extracted and RT-PCR analysis was performed either using mouse M-CSF (top) or human M-CSF (bottom) specific primers. RNA extracted either from mouse liver or human fetal liver served as positive controls for mouse and human primer pairs, respectively, no RT, and no template PCR reactions served as negative controls. Data are representative of 2 independent experiments. (C) Bone associated stromal cells from M-CSF$^{m/m}$, M-CSFm$^{m/h}$ and M-CSF$^{h/h}$ mice were isolated and cultured in vitro for 10 days, cells were lysed, and RNA was extracted and real time PCR analysis was performed either using mouse M-CSF (white) or human M-CSF (black) specific primers; mean values of duplicate samples are shown; error bars indicate±SEM; input cDNA quantity was normalized according to HPRT (hypoxanthine guanine phosphoribosyl transferase) expression levels; data are representative of 2 independent experiments; and, (D) bone associated stromal cells from M-CSF$^{m/m}$, M-CSFm$^{m/h}$ and M-CSF$^{h/h}$ mice were isolated and cultured in vitro for 10 days; cell culture supernatants were collected and the secreted levels of mouse (white) and human (black) M-CSF were quantified using species-specific M-CSF ELISA kits; mean values of triplicate samples are shown; error bars indicate±SEM; data are representative of 2 independent experiments. (E) M-CSF$^{m/m}$, M-CSF$^{h/m}$, and M-CSF$^{h/h}$ mice were bled and the serum levels of human and mouse M-CSF were quantified through ELISA. Shown are the mean values of triplicate samples. Error bars indicate±SEM.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Genetically modified mice comprising a nucleic acid sequence encoding a human M-CSF protein are provided. Also provided are genetically modified mice comprising a nucleic acid sequence encoding a human M-CSF protein that have been engrafted with human cells such as human hematopoietic cells, and methods for making such engrafted mice. These mice find use in a number of applications, such as in modeling human immune disease and pathogen infection; in in vivo screens for agents that modulate hematopoietic cell development and/or activity, e.g. in a healthy or a diseased state; in in vivo screens for agents that are toxic to hematopoietic cells; in in vivo screens for agents that prevent against, mitigate, or reverse the toxic effects of toxic agents on hematopoietic cells; in in vivo screens of human hematopoietic cells from an individual to predict the responsiveness of an individual to a disease therapy, etc.

Humanized M-CSF Mice

In some aspects of the invention, a humanized M-CSF mouse is provided. By a humanized M-CSF mouse, or "hM-CSF mouse", it is meant a mouse comprising a nucleic acid sequence that encodes a human M-CSF protein. By a human M-CSF protein, it is a meant a protein that is human M-CSF or is substantially identical to human M-CSF, e.g., it is 80% or more identical, 85% or more identical, 90% or more identical, or 95% or more identical to human M-CSF, for example, 97%, 98%, or 99% identical to human M-CSF. A nucleic acid sequence that encodes a human M-CSF protein is, therefore, a polynucleotide that comprises coding sequence for a human M-CSF protein, i.e. human M-CSF or a protein that is substantially identical to human M-CSF. M-CSF (also known as CSF-1, for "colony stimulating factor 1") is a cytokine that controls the production, differentiation, and function of macrophages. Polypeptide sequence for human M-CSF and the nucleic acid sequence that encodes for human M-CSF may be found at Genbank Accession Nos. NM_000757.5 (variant 1), NM_172210.2 (variant 2), and NM_172212.2 (variant 4). The genomic locus encoding the human M-CSF protein may be found in the human genome at Chromosome 1; NC_000001.10 (110453233-110472355). Protein sequence is encoded by exons 1 through 8 at this locus, while exon 9 comprises untranslated sequence. As such, a nucleic acid sequence comprising coding sequence for human M-CSF comprises one or more of exons 1-8 of the human M-CSF gene. In some instances, the nucleic acid sequence also comprises aspects of the genomic locus of the human M-CSF, e.g. introns, 3' and/or 5' untranslated sequence (UTRs). In some instances, the nucleic acid sequence comprises whole regions of the human M-CSF genomic locus. In some instances, the nucleic acid sequence comprises exon 2 of the human M-CSF genomic locus to 633 nt downstream of noncoding exon 9.

In the humanized M-CSF mice of the subject application, the nucleic acid sequence that encodes a human M-CSF protein is operably linked to one or more regulatory sequences of the mouse M-CSF gene. Mouse M-CSF regulatory sequences are those sequences of the mouse M-CSF genomic locus that regulate mouse M-CSF expression, for example, 5' regulatory sequences, e.g. the M-CSF promoter, M-CSF 5' untranslated region (UTR), etc.; 3' regulatory sequences, e.g. the 3'UTR; and enhancers, etc. Mouse M-CSF is located on chromosome 3 at about positions 107,543,966-107,563,387, and the mouse M-CSF coding sequence may be found at Genbank Accession Nos. NM_007778.4 (isoform 1), NM_001113529.1 (isoform 2), and NM_001113530.1 (isoform 3). The regulatory sequences of mouse M-CSF are well defined in the art, and may be readily identified using in silico methods, e.g. by referring to the above Genbank Accession Nos. on the UCSC Genome Browser, on the world wide web at genome.ucsc.edu, or by experimental methods as described below and in the art, e.g., Abboud et al. (2003) Analysis of the Mouse CSF-1 Gene Promoter in a Transgenic Mouse Model. J. Histochemistry and Cytochemistry 51(7):941-949, the disclosure of which is incorporated herein by reference. In some instances, e.g. when the nucleic acid sequence that encodes a human M-CSF protein is located at the mouse M-CSF genomic locus, the regulatory sequences operably linked to the human CSF coding sequence are endogenous, or native, to the mouse genome, i.e. they were present in the mouse genome prior to integration of human nucleic acid sequences.

In some instances, the humanized M-CSF mouse is generated by the random integration, or insertion, of human nucleic acid sequence encoding human M-CSF protein or a fragment thereof, i.e. "human M-CSF nucleic acid sequence", or "human M-CSF sequence", into the genome. Typically, in such embodiments, the location of the nucleic acid sequence encoding a human M-CSF protein in the genome is unknown. In other instances, the humanized M-CSF mouse is generated by the targeted integration, or insertion, of human M-CSF nucleic acid sequence into the genome, by, for example, homologous recombination. In homologous recombination, a polynucleotide is inserted into the host genome at a target locus while simultaneously removing host genomic material, e.g. 50 base pairs (bp) or more, 100 bp or more, 200 bp or more, 500 bp or more, 1 kB or more, 2 kB or more, 5 kB or more, 10 kB or more, 15 kB or more, 20 kB or more, or 50 kB or more of genomic material, from the target locus. So, for example, in a humanized M-CSF mouse comprising nucleic acid sequence that encodes a human M-CSF protein created by targeting human M-CSF nucleic acid sequence to the mouse M-CSF locus, human M-CSF nucleic acid sequence may replace some or all of the mouse sequence, e.g. exons and/or introns, at the M-CSF locus. In some such instances, human M-CSF nucleic acid sequence is integrated into the mouse M-CSF locus such that expression of the human M-CSF sequence is regulated by the native, or endogenous, regulatory sequences at the mouse M-CSF locus. In other words, the regulatory sequence(s) to which the nucleic acid sequence encoding a human M-CSF protein is operably linked are the native M-CSF regulatory sequences at the mouse M-CSF locus.

In some instances, the integration of human M-CSF sequence does not affect the transcription of the gene into which the human M-CSF sequence has integrated. For example, if the human M-CSF sequence integrates into coding sequence as an intein, or the human M-CSF sequence comprises a 2A peptide, the human M-CSF sequence will be transcribed and translated simultaneously with the gene into which the human M-CSF sequence has integrated. In other instances, the integration of the human M-CSF sequence interrupts the transcription of the gene into which the human M-CSF sequence has integrated. For example, upon integration of the human M-CSF sequence by homologous recombination, some or all of the coding sequence at the integration locus may be removed, such that the human M-CSF sequence is transcribed instead. In some such instances, the integration of human M-CSF sequence creates a null mutation, and hence, a null allele. A null allele is a mutant copy of a gene that completely lacks that gene's normal function. This can be the result of the complete absence of the gene product (protein, RNA) at the molecular level, or the expression of a non-functional gene product. At the phenotypic level, a null allele is indistinguishable from a deletion of the entire locus.

In some instances, the humanized M-CSF mouse comprises one copy of the nucleic acid sequence encoding a human M-CSF protein. For example, the mouse may be heterozygous for the nucleic acid sequence. In other words, one allele at a locus will comprise the nucleic acid sequence, while the other will be the endogenous allele. For example, as discussed above, in some instances, human M-CSF nucleic acid sequence is integrated into the mouse M-CSF locus such that it creates a null allele for mouse M-CSF. In some such embodiments, the humanized M-CSF mouse may be heterozygous for the nucleic acid sequence encoding, i.e. the humanized M-CSF mouse comprises one null allele for mouse M-CSF (the allele comprising the nucleic acid sequence) and one endogenous M-CSF allele (wild type or otherwise). In other words, the mouse is a M-CSF$^{h/m}$ mouse, where "h" represents the allele comprising the human sequence and "m" represents the endogenous allele. In other instances, the humanized M-CSF comprises two copies of the nucleic acid sequence encoding a human M-CSF protein. For example, the mouse may be homozygous for the nucleic acid sequence, i.e. both alleles for a locus in the diploid genome will comprise the nucleic acid sequence, i.e. the humanized M-CSF mouse comprises two null alleles for the mouse M-CSF (the allele comprising the nucleic acid sequence). In other words, the mouse is a M-CSF$^{h/h}$ mouse.

Strikingly, humanized M-CSF mice, e.g. such as those described above, e.g. M-CSF$^{h/h}$ and M-CSF$^{h/m}$ mice, exhibit normal, or wild type, development and function of macrophages and monocytes and tissues that develop from cells of the macrophage lineage, e.g., bone. For example, humanized mice normal teeth and bone properties as well as normal bone marrow content, myeloid cell frequencies in the bone marrow, spleen and peripheral blood, and macrophage frequencies in the bone marrow and spleen.

In some instances, the humanized M-CSF mouse comprises other genetic modifications. For example, the humanized M-CSF mouse may comprise at least one null allele for the Rag2 gene ("recombination activating gene 2", the coding sequence for which may be found at Genbank Accession No. 1.NM_009020.3). In some embodiments, the humanized M-CSF mouse comprises two null alleles for Rag2. In other words, the humanized M-CSF mouse is homozygous null for Rag2. As another example, the humanized M-CSF mouse comprises at least one null allele for the IL2rg gene ("interleukin 2 receptor, gamma", also known as the common gamma chain, or γC, the coding sequence for which may be found at Genbank Accession No. 1.NM_013563.3). In some embodiments, the humanized M-CSF mouse comprises two null alleles for IL2rg. In other words, the humanized M-CSF mouse is homozygous null for IL2rg. In some embodiments, the mouse comprises a null allele for both Rag2 and IL2rg, i.e. it is $Rag2^{-/-}$ $IL2RG^{-/-}$. Other genetic modifications are also contemplated. For example, the humanized M-CSF mouse may comprise modifications in other genes associated with the development and/or function of hematopoietic cells and the immune system, e.g. the replacement of one or other mouse genes with nucleic acid sequence encoding the human ortholog. Additionally or alternatively, the humanized M-CSF mouse may comprise modifications in genes associated with the development and/or function of other cells and tissues, e.g. genes associated with human disorders or disease, or genes that, when modified in mice, provide for mouse models of human disorders and disease.

In some aspects of the invention, the humanized M-CSF mouse, e.g. a $Rag2^{-/-}$ $IL2rg^{-/-}$ hM-CSF mouse or a sublethally irradiated hM-CSF mouse, is engrafted, or transplanted, with cells. Cells may be mitotic cells or post-mitotic cells, and include such cells of interest as pluripotent stem cells, e.g. ES cells, iPS cells, and embryonic germ cells; and somatic cells, e.g. fibroblasts, hematopoietic cells, neurons, muscle cells, bone cells, vascular endothelial cells, gut cells, and the like, and their lineage-restricted progenitors and precursors. Cell populations of particular interest include those that comprise hematopoietic stem or progenitor cells, which will contribute to or reconstitute the hematopoietic system of the humanized M-CSF mouse, for example, peripheral blood leukocytes, fetal liver cells, fetal bone, fetal thymus, fetal lymph nodes, vascularized skin, artery segments, and purified hematopoietic stem cells, e.g. mobilized HSCs or cord blood HSCs. Cells may be from any mammalian species, e.g. murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, may be harvested by apheresis, leukocytapheresis, density gradient separation, etc. As another example, cells, e.g. skin, muscle, bone marrow, spleen, liver, pancreas, lung, intestine, stomach tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

In some instances, a heterogeneous population of cells will be transplanted into the humanized mouse. In other instances, a population of cells that is enriched for a particular type of cell, e.g. a progenitor cell, e.g. a hematopoietic progenitor cell, will be engrafted into the humanized mouse. Enrichment of a cell population of interest may be by any convenient separation technique. For example, the cells of interest may be enriched by culturing methods. In such culturing methods, particular growth factors and nutrients are typically added to a culture that promote the survival and/or proliferation of one cell population over others. Other culture conditions that affect survival and/or proliferation include growth on adherent or non-adherent substrates, culturing for particular lengths of time, etc. Such culture conditions are well known in the art. As another example, cells of interest may be enriched for by separation the cells of interest from the initial population by affinity separation techniques. Techniques for affinity separation may include magnetic separation using magnetic beads coated with an affinity reagent, affinity chromatography, "panning" with an affinity reagent attached to a solid matrix, e.g. plate, cytotoxic agents joined to an affinity reagent or used in conjunction with an affinity reagent, e.g. complement and cytotoxins, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells of interest.

For example, using affinity separation techniques, cells that are not the cells of interest for transplantation may be depleted from the population by contacting the population with affinity reagents that specifically recognize and selectively bind markers that are not expressed on the cells of interest. For example, to enrich for a population of hematopoietic progenitor cells, one might deplete cells expressing mature hematopoietic cell markers. Additionally or alternatively, positive selection and separation may be performed using by contacting the population with affinity reagents that specifically recognize and selectively bind markers associated with hematopoietic progenitor cells, e.g. CD34, CD133, etc. By "selectively bind" is meant that the molecule binds preferentially to the target of interest or binds with greater affinity to the target than to other molecules. For example, an antibody will bind to a molecule comprising an epitope for which it is specific and not to unrelated epitopes. In some embodiments, the affinity reagent may be an antibody, i.e. an antibody that is specific for CD34, CD133, etc. In some embodiments, the affinity reagent may be a specific receptor or ligand for CD34, CD133, etc., e.g. a peptide ligand and receptor; effector and receptor molecules, a T-cell receptor specific for CD34, CD133, etc., and the like. In some embodiments, multiple affinity reagents specific for the marker of interest may be used.

Antibodies and T cell receptors that find use as affinity reagents may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Of particular interest is the use of labeled antibodies as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The initial population of cells are contacted with the affinity reagent(s) and incubated for a period of time sufficient to bind the available cell surface antigens. The incubation will usually be at least about 5 minutes and usually less than about 60 minutes. It is desirable to have a sufficient concentration of antibodies in the reaction mixture, such that the efficiency of the separation is not limited by lack of antibody. The appropriate concentration is determined by titration, but will typically be a dilution of antibody into the volume of the cell suspension that is about 1:50 (i.e., 1 part antibody to 50 parts reaction volume), about 1:100, about 1:150, about 1:200, about 1:250, about 1:500, about 1:1000, about 1:2000, or about 1:5000. The medium in which the cells are suspended will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc.

The cells in the contacted population that become labeled by the affinity reagent are selected for by any convenient affinity separation technique, e.g. as described above or as known in the art. Following separation, the separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for a cell type of interest, e.g. hematopoietic cells, are achieved in this manner. The cells will be about 70%, about 75%, about 80%, about 85% about 90% or more of the cell composition, about 95% or more of the enriched cell composition, and will preferably be about 95% or more of the enriched cell composition. In other words, the composition will be a substantially pure composition of cells of interest.

The cells to be transplanted into the humanized M-CSF mouse, be they a heterogeneous population of cells or an enriched population of cells, may be transplanted immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells. Additionally or alternatively, the cells may be cultured in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The cells may be genetically modified prior to transplanting to the humanized M-CSF mouse, e.g. to provide a selectable or traceable marker, to induce a genetic defect in the cells (e.g. for disease modeling), to repair of a genetic defect or ectopically express a gene in the cells (e.g. to determine if such modifications will impact the course of a disease), etc. Cells may be genetically modified by transfection or transduction with a suitable vector, homologous recombination, or other appropriate technique, so that they express a gene of interest, or with an antisense mRNA, siRNA or ribozymes to block expression of an undesired gene. Various techniques are known in the art for the introduction of nucleic acids into target cells. To prove that one has genetically modified the cells, various techniques may be employed. The genome of the cells may be restricted and used with or without amplification. The polymerase chain reaction; gel electrophoresis; restriction analysis; Southern, Northern, and Western blots; sequencing; or the like, may all be employed. General methods in molecular and cellular biochemistry for these and other purposes disclosed in this application can be found in such standard textbooks as Molecular Cloning: A Laboratory Manual, 3rd Ed. (Sambrook et al., Cold Spring Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

The cells may be transplanted in the humanized M-CSF mouse by any convenient method, including, for example, intra-hepatic injection, tail-vein injection, retro-orbital injection, and the like. Typically, about $0.5 \times 10^5$-$2 \times 10^6$ pluripotent or progenitor cells are transplanted, e.g. about $1 \times 10^5$-$1 \times 10^6$ cells, or about $2 \times 10^5$-$5 \times 10^5$ cells. In some instances, the mouse is sublethally irradiated prior to transplanting the human cells. In other words, the mouse is exposed to a sublethal dose of radiation, e.g. as described in the examples section below and as well-known in the art. The engrafted humanized M-CSF mouse is then maintained under laboratory animal husbandry conditions for at least 1 week, e.g. 1 week or more, or two weeks or more, sometimes 4 weeks or more, and in some instances 6 weeks or more, to allow sufficient reconstitution of the immune system with the engrafted cells.

As demonstrated in the examples section below, humanized M-CSF mice demonstrate a significantly increased ability to engraft and maintain human hematopoietic cells as compared to other mouse strains that have been developed for this purpose and other M-CSF transgenic mice. For example, intra-hepatic transfer of human fetal liver-derived hematopoietic stem and progenitor cells (CD34$_+$) to newborn mice results in more efficient differentiation and enhanced frequencies of human monocytes/macrophages in bone marrow, spleen, peripheral blood, lungs, liver and the peritoneal cavity. Significant proportions of human CD14$_+$CD33$_+$ cells are observed at 16-20 weeks. Specifically, humanized M-CSF mice engrafted with hematopoietic cells demonstrate one or more, in some instances two or more, in some instances, three or more, in some instances four or more, in some instances all of the following characteristics: they express human M-CSF in bone marrow, spleen, blood, liver, brain, lung, testis and kidney at a level comparable to expression of mouse M-CSF in a wild-type mouse; exhibit a frequency of hCD14$^+$CD33$^+$ cells of spleen that is 2- to 6-fold higher than hCD14$^+$CD33$^+$ in an engrafted mouse that does not express hM-CSF; exhibit a frequency in hCD14$^+$CD33$^+$ cells of peripheral blood that is 2- to 8-fold higher than hCD14$^+$CD33$^+$ in an engrafted mouse that does not express hM-CSF; exhibit a level of hCD14$^+$CD33$^+$ monocyte/macrophage lineage cells in blood of about 15 to about 40%; exhibit a level of hCD14$^+$CD33$^+$ monocyte/macrophage lineage cells in blood of about 5 to about 15% at about 20 weeks of age; exhibit a response to LPS injection that is about 1.5- to about 6-fold greater with respect to percentage of hCD14$^+$CD33$^+$ cells in liver than mice that lack a human M-CSF; exhibit an enhanced production of hCD14$^+$CD33$^+$hCD45$^+$ cells in spleen about 48 hours following LPS injection, wherein the enhancement is about 2- to about 5-fold over an engrafted mouse that lacks hM-CSF; exhibit an enhanced production of serum human IL-6 in response to LPS, wherein the level of hIL-6 about 6 hours after LPS injection is enhanced about 2- to about 5-fold over an engrafted mouse that lacks a hM-CSF; exhibit in vitro secretion by a monocyte and/or macrophage upon LPS stimulation that is about 2- to 3-fold higher with respect to hTNFα than an engrafted mouse that lacks a hM-CSF gene; exhibit in vitro secretion by a monocyte and/or macrophage upon LPS stimulation that is about 2- to 4-fold higher with respect to hIL-6 than an engrafted mouse that lacks a hM-CSF gene; exhibit in vitro secretion by a monocyte and/or macrophage upon I:C stimulation that is about 3- to 6-fold higher with respect to hIFNα than an engrafted mouse that lacks a hM-CSF gene; exhibit in vitro secretion by a monocyte and/or macrophage upon I:C stimulation that is about 2- to 3-fold higher with respect to hIFNβ than an engrafted mouse that lacks a hM-CSF gene; exhibit enhanced phagocytosis as compared with a genetically modified and engrafted mouse that lacks a hM-CSF gene; exhibit enhanced chemotaxis in vitro in response to Mip3β as compared with a genetically modified engrafted mouse that lacks a hM-CSF gene; and; exhibit upregulation in vitro of a co-stimulatory molecule in response to LPS stimulation, wherein the co-stimulatory molecule is selected from human CD40, human CD80, human CD86, human HLA-DR, and a combination thereof.

Utility

The humanized M-CSF mice and humanize M-CSF mice engrafted with human hematopoietic cells, e.g. engrafted Rag2$^{-/-}$ IL2rg$^{-/-}$ hM-CSF mice, and optionally other genetic modifications are useful in many applications. For example, these mice provide a useful system for modeling human immune diseases and human pathogens. For example, the subject mice are useful for modeling a human hematopoietic malignancy that originates from an early human hematopoietic cell, e.g. from a human hematopoietic stem or progenitor cell. As another example, the subject mice are useful for studying human pathogens, e.g. viruses, fungi, and bacteria, that do not normally infect mice.

One such example of a human pathogen that does not normally infect mice is the causative agent of typhoid fever, S. typhi. Typhoid fever afflicts over 21 million people around the world—principally in the developing world—including about 400 cases/year in the United States. Typhoid fever has been treated with the drugs amoxicillin, ampicillin, cefotaxime, ceftriaxone, ceftazidime, chloramphenicol, ciprofloxacin, co-trimoxazole, ertapenem, imipenem, fluoroquinolones (e.g., ciprofloxacin, gatifloxacin, ofloxacin), streptomycin, sulfadiazine, sulfamethoxazole, tetracycline, and combinations thereof. Recurrent infections are common, which limits disease management by antibiotic therapy. Further, multi-drug resistance is also prevalent with S. typhi infections.

New therapeutics, new vaccines, and new ways of testing efficacy of therapeutics and vaccines are needed. A mouse capable of being infected by S. typhi, for example, would be useful to identify new therapeutics and new vaccines. New therapeutics and new vaccines could be testing in such a mouse by, e.g., determining the amount of S. typhi in the mouse (in blood or a given tissue) in response to treatment with a putative anti-S. typhi agent, or by inoculating the mouse with a putative vaccine followed by exposure to an infective administration of S. typhi, and observing any change in infectivity due to inoculation by the putative vaccine as compared to a control not inoculated with the vaccine but infected with S. typhi.

A humanized M-CSF mouse engrafted with human hematopoietic cells, e.g. a Rag2$^{-/-}$ IL2rg$^{-/-}$ hM-CSF mouse, is useful for studying human pathogens, i.e. pathogens that infect humans; the response of the human immune system to infection by human pathogens; and the effectiveness of agents in protecting against and/or treating infection by human pathogens. The pathogen may be a virus, a fungus, a bacterium, etc. Non-limiting examples of viral pathogens include human or porcine or avian influenza virus. Non-limiting examples of bacterial pathogens include mycobacterium, e.g. *Mycobacterium tuberculosis* (*M. tuberculosis*), and enterobacterium, e.g. *Salmonella typhi* (*S. typhi*).

For example, engrafted humanized M-CSF mice are useful as a non-human animal model of S. typhi infection. By contrast, wild-type mice, and other known immune-compromised mice (e.g., RAG1/RAG2 gene knockout mice), are not capable of being infected by S. typhi. As discussed above, engrafted human M-CSF mice as described herein display an enhanced engraftment of human cells as compared to an engrafted mice that do not comprise a human M-CSF protein. This enhancement is sufficient to maintain a productive S. typhi infection, that is, the S. typhi is able to reproduce in the mouse, i.e. the infected mouse is able to harbor and reproduce S. typhi in one or more of its cells. In a specific embodiment, the mouse is capable of reproducing S. typhi at least a week, 10 days, two weeks, three weeks, or four weeks following an initial introduction or infective exposure of S. typhi In other words, the mouse is capable of maintaining a S. typhi titer or level in its blood or in at least one tissue for at least a week, 10 days, two week, three weeks, or four weeks following an infective exposure to S. typhi. Examples of methods for infecting mice with S. typhi and for assessing infection may be found in, for example, US Published Application No. 2011/0200982, the disclosure of which is incorporated herein by reference.

As another example, engrafted humanized M-CSF mice, e.g. engrafted Rag2$^{-/-}$ IL2rg$^{-/-}$ hM-CSF mice, are useful as a non-human animal model of infection by *M. tuberculosis*. The enhanced engraftment of human hematopoietic cells in mice comprising a nucleic acid that encodes human M-CSF protein is sufficient to maintain a productive *M. tuberculosis* infection, that is, the *M. tuberculosis* is able to reproduce in the mouse, i.e. the infected mouse is able to harbor and reproduce *M. tuberculosis* in one or more of its cells. In some such embodiments, the mouse mounts an anti-mycobacterial immune response to a human pathogenic mycobacterium, wherein the response comprises formation of a granuloma mediated by human immune cells and that comprises a human immune cell. In some such embodiments, the granuloma is a lung granuloma. In some such embodiments, the granuloma is a well-defined granuloma. Examples of methods for infecting mice with *M. tuberculosis* and for assessing infection may be found in, for example, US Published Application No. 2011/0200982, the disclosure of which is incorporated herein by reference.

Other examples of human pathogens that do not infect a mouse expressing human M-CSF and in some instances, one or more other genetic modifications e.g. as described herein, or that infect wild-type mice, wherein the wild-type mouse following infection does not model an immune response that a human mounts in response to the pathogen, will be well-known to the ordinarily skilled artisan.

Such mouse models of pathogen infection are useful in research, e.g. to better understand the progression of human infection. Such mouse models of infection are also useful in drug discovery, e.g. to identify candidate agents that protect against or treat infection.

Humanized M-CSF mice engrafted with human hematopoietic cells provide a useful system for screening candidate agents for other desired activities in vivo as well, for example, for agents that are able to modulate (i.e., promote or suppress) hematopoietic cell development and/or activity, e.g. the activity of B cells, T cells, NK cells, macrophages, neutrophils, eosinophils, basophils, etc., e.g. in a healthy or a diseased state, e.g. to identify novel therapeutics and/or develop a better understanding of the molecular basis of the development and function of the immune system; for agents that are toxic to hematopoietic cells, e.g. B cells, T cells, NK cells, macrophages, neutrophils, eosinophils, basophils, etc., and progenitors thereof; and for agents that prevent against, mitigate, or reverse the toxic effects of toxic agents on hematopoietic cells, e.g. B cells, T cells, NK cells, macrophages, neutrophils, eosinophils, basophils, etc., and progenitors thereof; etc. As yet another example, the genetically modified mice described herein provide a useful system for predicting the responsiveness of an individual to a disease therapy, e.g. by providing an in vivo platform for screening the responsiveness of an individual's immune system to an agent, e.g. a therapeutic agent, to predict the responsiveness of an individual to that agent.

In screening assays for biologically active agents, humanized M-CSF mice, e.g. Rag2$^{-/-}$ IL2rg$^{-/-}$ hM-CSF mice, that have been engrafted with human hematopoietic cells and in some instances, infected with human pathogens, or cells to be engrafted into a humanized M-CSF mouse, are contacted with a candidate agent of interest and the effect of the candidate agent is assessed by monitoring one or more output parameters. These output parameters may be reflective of the viability of the cells, e.g. the total number of hematopoietic cells or the number of cells of a particular hematopoietic cell type, or of the apoptotic state of the cells, e.g. the amount of DNA fragmentation, the amount of cell blebbing, the amount of phosphatidylserine on the cell surface, and the like by methods that are well known in the art. Alternatively or additionally, the output parameters may be reflective of the differentiation capacity of the cells, e.g. the proportions of differentiated cells and differentiated cell types. Alternatively or additionally, the output parameters may be reflective of the function of the cells, e.g. the cytokines and chemokines produced by the cells, the ability of the cells to home to and extravasate to a site of challenge, the ability of the cells to modulate, i.e. promote or suppress, the activity of other cells in vitro or in vivo, etc. Other output parameters may be reflective of the extent of pathogen infection in the animal, e.g. the titer of pathogen in the mouse, the presence of granuloma in the mouse, etc.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, vaccines, antibiotics or other agents suspected of having antibiotic properties, peptides, polypeptides, antibodies, agents that have been approved pharmaceutical for use in a human, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the pluripotent cells are contacted with vectors comprising the nucleic acid of interest such that the vectors are taken up by the cells.

Methods for contacting cells, e.g. cells in culture or cells in a mouse, with nucleic acid vectors, such as electroporation, calcium chloride transfection, and lipofection, are well known in the art. Alternatively, the nucleic acid of interest may be provided to the cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the cells of interest—in some instance, the engrafted cells, in some instance, the cells of the host, i.e. the humanized M-CSF—are targeted by the packaged viral particles.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Additionally or alternatively, such polypeptides may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or non-covalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The candidate polypeptide agent may be produced from eukaryotic cells, or may be produced by prokaryotic cells. It may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by administering the agent to at least one and usually a plurality of samples, sometimes in conjunction with samples lacking the agent. The change in parameters in response to the agent is measured, and the result evaluated by comparison to reference cultures, e.g. in the presence and absence of the agent, obtained with other agents, etc. In instances in which a screen is being performed to identify candidate agents that will prevent, mitigate or reverse the effects of a toxic agent, the screen is typically performed in the presence of the toxic agent, where the toxic agent is added at the time most appropriate to the results to be determined. For example, in cases in which the protective/preventative ability of the candidate agent is tested, the candidate agent may be added before the toxic agent, simultaneously with the candidate agent, or subsequent to treatment with the candidate agent. As another example, in cases in which the ability of the candidate agent to reverse the effects of a toxic agent is tested, the candidate agent may be added subsequent to treatment with the candidate agent. As mentioned above, in some instances, the sample is the humanized M-CSF mouse that has been engrafted with cells, i.e. candidate agent provided to the humanized M-CSF mouse that has been engrafted with cells. In some instances, the sample is the cells to be engrafted, i.e. the candidate agent is provided to cells prior to transplantation.

If the candidate agent is to be administered directly to the mouse, the agent may be administered by any of a number of well-known methods in the art for the administration of peptides, small molecules and nucleic acids to mice. For example, the agent may be administered orally, mucosally, topically, intrdermally, or by injection, e.g. intraperitoneal, subcutaneous, intramuscular, intravenous, or intracranial injection, and the like. The agent may be administered in a buffer, or it may be incorporated into any of a variety of formulations, e.g. by combination with appropriate pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. The agent may be systemic after administration or may be localized by the use of regional administration, intramural administration, or use of an implant that acts to retain the active dose at the site of implantation. The active agent may be formulated for immediate activity or it may be formulated for sustained release. For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. A BBB disrupting agent can be co-administered with the agent when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

If the agent(s) are provided to cells prior to transplantation, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

An analysis of the response of cells in the humanized M-CSF mouse to the candidate agent may be performed at any time following treatment with the agent. For example, the cells may be analyzed 1, 2, or 3 days, sometimes 4, 5, or 6 days, sometimes 8, 9, or 10 days, sometimes 14 days, sometimes 21 days, sometimes 28 days, sometimes 1 month or more after contact with the candidate agent, e.g. 2 months, 4 months, 6 months or more. In some embodiments, the analysis comprises analysis at multiple time points. The selection of the time point(s) for analysis will be based upon the type of analysis to be performed, as will be readily understood by the ordinarily skilled artisan.

The analysis may comprise measuring any of the parameters described herein or known in the art for measuring cell viability, cell proliferation, cell identity, cell morphology, and cell function, particularly as they may pertain to cells of the immune cells. For example, flow cytometry may be used to determine the total number of hematopoietic cells or the number of cells of a particular hematopoietic cell type. Histochemistry or immunohistochemistry may be performed to determine the apoptotic state of the cells, e.g. terminal deoxynucleotidyl transferase dUTP nick end labeling (TUNEL) to measure DNA fragmentation, or immunohistochemistry to detect Annexin V binding to phosphatidylserine on the cell surface. Flow cytometry may also be employed to assess the proportions of differentiated cells and differentiated cell types, e.g. to determine the ability of hematopoietic cells to differentiate in the presence of agent. ELISAs, Westerns, and Northern blots may be performed to determine the levels of cytokines, chemokines, immunoglobulins, etc. expressed in the engrafted humanized M-CSF mice, e.g. to assess the function of the engrafted cells. In vivo assays to test the function of immune cells, as well as assays relevant to particular diseases or disorders of interest such as diabetes, autoimmune disease, graft v. host disease, AMD, etc. may also be performed. See, e.g. Current Protocols in Immunology (Richard Coico, ed. John Wiley & Sons, Inc. 2012) and Immunology Methods Manual (I. Lefkovits ed., Academic Press 1997), the disclosures of which are incorporated herein by reference.

So, for example, a method is provided for determining the effect of an agent on a human pathogen is provided, comprising exposing an engrafted humanized M-CSF mouse, e.g. an engrafted Rag2$^{-/-}$ IL2rg$^{-/-}$ hM-CSF mouse, to an effective amount of a human pathogen, the effective amount of a pathogen being the amount of pathogen required to produce an infection in the mouse; allowing the pathogen to infect the mouse; measuring a parameter of the infection over time in the presence of the agent; and comparing that measurement to the measurement from an engrafted humanized M-CSF mouse not exposed to the agent. The agent is determined to be an antipathogenic, e.g. anti-*S. typhi*, agent if it reduces the amount of the agent in blood or a tissue of the mouse by at least half following a single administration or two or more administrations of the agent over a selected period of time.

As another example, a method is provided for determining if a pathogen isolate or strain of interest is drug resistant, e.g. multidrug resistant. In these methods, an engrafted humanized M-CSF mouse, e.g. an engrafted Rag2$^{-/-}$ IL2rg$^{-/-}$ hM-CSF mouse, is exposed to an effective amount of a human pathogen isolate or strain of interest, the effective amount of the pathogen being the amount of pathogen required to produce an infection in the mouse; the pathogen is allowed to infect the mouse; a parameter of the infection, e.g. the titer of the isolate or strain of interest in the blood or tissue of the mouse, the ability of the isolate or strain of interest to maintain an infection in the mouse, or the ability of the isolate or strain of interest to reproduce in the mouse at a point in time after administration of the drug, is measured in the presence of the drug; and that measurement is compared to the measurement from an engrafted humanized M-CSF mouse infected with pathogen not exposed to the agent. Examples of drugs of interest include amoxicillin, ampicillin, cefotaxime, ceftriaxone, ceftazidime, chloramphenicol, ciprofloxacin, co-trimoxazole, ertapenem, imipenem, fluoroquinolones (e.g., ciprofloxacin, gatifloxacin, ofloxacin), streptomycin, sulfadiazine, sulfamethoxazole, tetracycline, and a combination thereof. In a specific embodiment, the administration of the drug or combination of drugs is at least a week, 10 days, two week, three weeks, or four weeks after an infection-producing exposure to the isolate or strain of interest.

Other examples of uses for the subject mice are provided elsewhere herein. Additional applications of the genetically modified and engrafted mice described in this disclosure will be apparent to those skilled in the art upon reading this disclosure.

Reagents, Devices and Kits

Also provided are reagents, devices and kits thereof for practicing one or more of the above-described methods. The subject reagents, devices and kits thereof may vary greatly.

In some embodiments, the reagents or kits will comprise one or more agents for use in the methods described. For example, the kit may comprise a humanized M-CSF mouse. The kit may comprise reagents for breeding humanized M-CSF mice, e.g. primers and, in some instances, reagents for genotyping humanized M-CSF mice. The kit may comprise human hematopoietic cells or an enriched population of human hematopoietic progenitor cells for transplantation into the humanized M-CSF mouse, or reagents for preparing a population of hematopoietic cells or an enriched population of hematopoietic cells from a human for transplantation into a humanized M-CSF mouse. Other reagents may include reagents for determining the viability and/or function of hematopoietic cells, e.g. in the presence/absence of candidate agent, e.g. one or more antibodies that are specific for markers expressed by different types of hematopoietic cells, or reagents for detecting particular cytokines, chemokine, etc. Other reagents may include culture media, culture supplements, matrix compositions, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Colony Stimulating Factor-1 (CSF-1) or Macrophage Colony Stimulating Factor (M-CSF) is one of the early cytokines that was discovered to promote hematopoiesis. In the hematopoietic system, M-CSF is believed to act specifically on myeloid progenitors, starting from the common myeloid progenitor (CMP) stage, and to favor the differentiation of CMPs into the monocyte/macrophage lineage (Sherr, C. J. et al. (1988) Macrophage colony-stimulating factor, CSF-1, and its proto-oncogene-encoded receptor, Cold Spring Harb. Symp. Quant. Biol. 53 Pt 1:521-530). In addition, M-CSF is necessary for the survival, adhesion and motility of macrophages (Pixley, F. J., and Stanley, E. R. (2004) CSF-1 regulation of the wandering macrophage: complexity in action, Trends Cell Biol. 14:628-638; Socolovsky, M. et al. (1998) Cytokines in hematopoiesis: specificity and redundancy in receptor function, Adv. Protein Chem. 52:141-198; Stanley, E. R. et al. (1997) Biology and action of colony—stimulating factor-1, Mol. Reprod. Dev. 1997; 46:4-10). Other than its key role in myeloid differentiation, M-CSF is vital for the differentiation of osteoclasts, for the differentiation, survival and proliferation of the cells of female reproductive tract, and for the formation of placenta (Pixley et al. (2004); Socolovsky et al. (1998); Stanley et al. (1997)). M-CSF is produced by a variety of cells including fibroblasts, bone marrow (BM) stromal cells, activated T cells and macrophages, and secretory epithelial cells. M-CSF signals through the M-CSF receptor (Fms; CD115) and ligation of its receptor by M-CSF results in tyrosine phosphorylation of Fms and subsequent phosphorylation of several host cell proteins, such as Grb2, Shc, Sos1 and p85 (Pixley et al. (2004); Stanley et al. (1997); Rohrschneider, L. R. et al. (1997) Growth and differentiation signals regulated by the M-CSF receptor, Mol. Reprod. Dev. 46:96-103; Yeung, Y. G. and Stanley, E. R. (2003) Proteomic approaches to the analysis of early events in colony-stimulating factor-1 signal transduction, Mol. Cell. Proteomics 2:1143-1155).

The inventors hypothesized that the defective human myeloid differentiation in the humanized mice might be due to the lack of specific signals that promote myeloid differentiation. To validate this, the inventors engineered a new generation of humanized mice to secrete human M-CSF at physiological levels from the appropriate tissues. Analysis of these humanized M-CSF mice revealed normal expression, both qualitatively and quantitatively, of human M-CSF. Analysis of humanized M-CSF mice engrafted with human CD34$^+$ cells indicated augmented frequencies of human monocytes/macrophages in various tissues. Furthermore, human monocytes/macrophages obtained from these mice exhibited enhanced functional properties.

Humanized M-CSF mice described herein show augmented frequencies and functions of human myeloid cells. Insertion of human M-CSF into the mouse M-CSF locus of Balb/c mice deficient for recombination activating gene 2 (Rag2; Genbank Accession No. 1.NM_009020.3) and gamma chain (γc, also known as "Interleukin 2 receptor, gamma chain" or IL2RG; Genbank Accession No. 1.NM_013563.3) (Balb/c Rag2$^{-/-}$ γ$^{-/-}$ mice) resulted in faithful expression of human M-CSF in these mice both qualitatively and quantitatively. Intra-hepatic transfer of human fetal liver-derived hematopoietic stem and progenitor cells (CD34$^+$) in humanized M-CSF (M-CSF$^{h/h}$) newborn pups resulted in more efficient differentiation and enhanced frequencies of human monocytes/macrophages in the bone marrow, spleen, and peripheral blood. In addition, M-CSF$^{h/h}$ mice exhibited sustained abilities to support human monocyte/macrophage differentiation even after 20 weeks of transplantation. Moreover, M-CSF$^{h/h}$ mice contain resident human monocytes/macrophages within various tissues, including liver and lungs, unlike control unmodified mice. Human monocytes/macrophages obtained from the humanized M-CSF mice also show augmented functional properties such as migration, phagocytosis, activation and responses to LPS.

Example 1

Cell Preparations, Analytical Methods, and Assays

CD34$^+$ Cell Isolation and Transplantation.

Human Fetal Liver Samples were obtained from the human fetal liver tissue repository at the Albert Einstein College of Medicine, Bronx, N.Y. and from the Advance Biosciences Resources, Inc., Alameda, Calif. All experiments involving human tissues were performed under the approval of the Yale Human Investigations Committee.

For isolating human CD34$^+$ cells, fetal liver samples were rinsed once with PBS and cut into small pieces, treated with collagenase D (100 ng/mL) at 37° C. for 45 minutes. Single cell suspensions were prepared and the mononuclear cells were isolated using density gradient centrifugation (lymphocyte separation medium, MP biomedicals). CD34$^+$ cells were isolated after treating the cells with anti-human CD34 microbeads followed by MACS™ technique (Miltenyi Biotech).

For transplantation, new born pups (day 1 of birth) were sublethally irradiated with two separate doses (2×150 cGy) 4 hours apart and 1×10$^5$ to 2×10$^5$ purified human CD34$^+$ cells in 20 uL of PBS were injected into the liver using a 22-gauge needle (Hamilton Company, Reno, Nev.).

Mesenchymal Stroma Cell (MSC) Isolation and Culture.

Long bones of mice were isolated and the BM cells were flushed out. Bones were cut into pieces and digested with a cocktail of collagenase D and P (25 ng/mL) for 45 minutes at 37° C. Suspension cells were isolated and plated in the presence of MSC culture medium (Stem Cell Technologies). After 2 weeks of culture, CD45$^-$Sca1$^+$CD90$^+$ cells were isolated and cultured.

Antibodies and Flow Cytometry.

Single cell suspensions were analyzed by flow cytometry using FACS Calibur or LSRII and CELLQUEST™ software, FACS DIVA™ software (BD Biosciences, San Jose, Calif.) or FLOWJO™ software (Tree Star, Inc., Ashland, Oreg.), respectively. Cell sorting of defined subpopulations was performed using a FACS ARIA™ cell sorter (BD Biosciences, San Jose, Calif.).

The following human antibodies were used in the study: CD11b, CD14, CD33, CD34, CD38, CD40, CD45, CD80, CD86, CD90 and HLA-DR.

The following mouse antibodies were used in this study: CD11b, CD40, CD45, CD80, CD86, F4/80, Gr1, H2K$^d$ and IA$^d$.

Cell Culture.

For murine macrophage differentiation, BM cells were plated in 6 well plates in the presence of DMEM with 10% FCS and necessary supplements (2 mM L-Glutamine, 1% Penicillin-Streptomycin and 1 mM nonessential amino acids). Cells were treated with either recombinant murine M-CSF (10 ng/mL) or recombinant human M-CSF (10 ng/mL) for 7 days. Cell culture supernatant was removed every third day and culture was replaced with fresh medium and cytokines.

For human macrophage studies, such as activation, phagocytosis and migration, $2\times10^5$ CD45$^+$CD14$^+$CD33$^+$ cells of the spleens were sorted and cultured in vitro in the DMEM with 15% human AB serum and necessary supplements (2 mM L-Glutamine, 1% Penicillin-Streptomycin and 1 mM nonessential amino acids).

Activation, Phagocytosis and Migration Assays.

For LPS stimulation in vivo, mice were injected i.p. with LPS (100 ng/g body weight). For LPS stimulation in vitro, LPS (10 ng/mL) was added to the cells and cultured for either 1 or 2 days. For poly I:C stimulation in vitro, cells were cultured in the presence of poly I: C (10 ug/mL) for either 6 or 12 hours.

Phagocytosis assay was performed using the commercially available VYBRANT™ phagocytosis assay kit (Invitrogen) according to the manufacturer's instructions.

Migration assays were performed using a commercially available QCM™ chemotaxis cell migration assays kit (Millipore) according to the manufacturer's instructions.

RNA Extraction and Real Time PCR.

Total RNA was isolated using commercially available kit systems (RNEASY™ Mini kit, Qiagen). cDNA was synthesised using oligo dT primer and expand reverse transcriptase (Roche). The PCR reaction was performed in duplicates using 7500 real time PCR systems and power SYBR™ Green PCR master mix (Applied Biosystems) according to the manufacturer's instructions using the following gene specific primer pairs: Human CSF1 (sense: 5'-TACTGTAGCCACAT-GATTGGGA-3' (SEQ ID NO:1) and antisense: 5'-CCTGT-GTCAGTCAAAGGAAC-3' (SEQ ID NO:2)), Mouse csf1 (sense: 5'-CGACATGGCTGGGCTCCC-3' (SEQ ID NO:3) and antisense: 5'-CGCATGGTCTCATCTATTAT-3' (SEQ ID NO:4), Human IFNa (sense: 5'-GTACTGCAGAATCTCTC-CTTTCTCCTG-3' (SEQ ID NO:5) and antisense: 5'-GT-GTCTAGATCTGACAACCTCCCAGGCACA-3' (SEQ ID NO:6)), Human IFNb (sense: 5'-TTGTGCTTCTCCACTA-CAGC-3' (SEQ ID NO:7) and antisense: 5'-CTGTAAGTCT-GTTAATGAAG-3' (SEQ ID NO:8)), Mouse hprt primers (sense: 5'-AAGGACCTCTCGAAGTGTTGGATA (SEQ ID NO:9) and antisense: 5'-CATTTAAAAGGAACTGTTGA-CAACG-3' (SEQ ID NO:10)) and Human HPRT primers (sense: 5'-CTTCCTCCTCCTGAGGAGTC-3' (SEQ ID NO:11) and antisense: 5'-CCTGACCAAGGAAAG-CAAAG-3' (SEQ ID NO:12)). For normal PCR, DNA of the target cells was extracted using a commercially available kit (DNEASY™ blood and tissue kit, Qiagen) and PCR analysis was performed using gene specific primer pairs.

ELISA.

For cytokine quantification studies, either blood serum or cell culture supernatants were collected and subjected to the ELISA using commercially available human IL6 and human TNF ELISA kits (Ray Biotech, Inc., GA) according to the manufacturer's instructions.

Histology.

Solid organs were fixed in 4% PFA. Fixed organs were embedded in paraffin (Blue RiBbon; Surgipath Medical Industries). Blocks were sectioned and the 5-µm sections were stained with H&E stain, followed by placement of coverslips by routine methods. Sections were maintained without any medium. Digital light microscopic images were recorded, at room temperature, with a Zeiss Axio Imager.A1 microscope (with 2× and 10× objective lenses), AxioCam MRc5 camera, and AxioVision 4.7.1 imaging software (Carl Zeiss Microimaging LLC).

Statistical Analysis.

Data are presented as mean±SEM. Statistical significance was assessed using a 2-sided Student t test. P values >0.05 were considered to be nonsignificant and P values <0.05 were represented as *.

Example 2

Genetically Modified Mice for Engraftment

Figure 8:
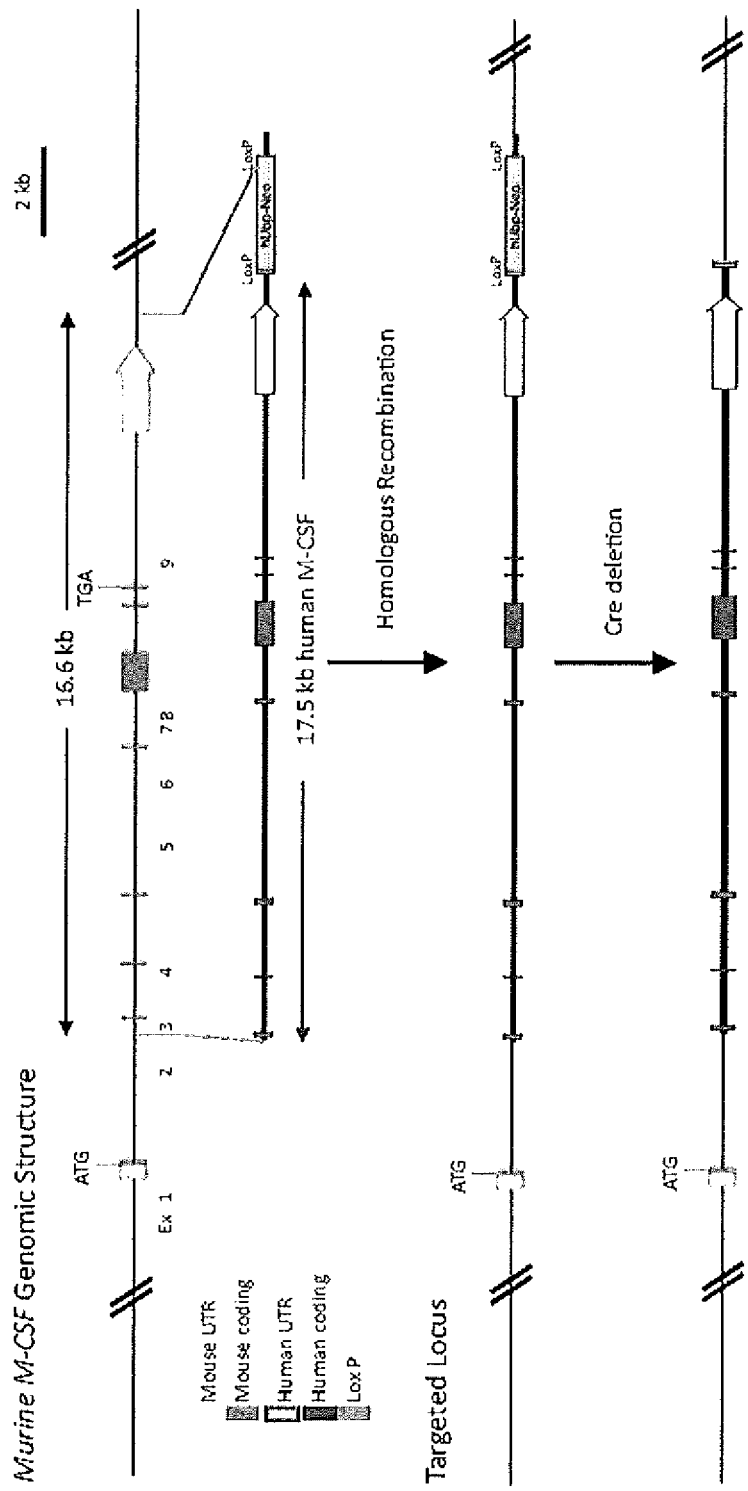
FIG. 8 provides a schematic representation of the mouse M-CSF locus indicating the relative location of the exons 1-9, and final targeted allele with human M-CSF gene.

Human M-CSF Knockin Strategy. A targeting construct for replacing the mouse M-CSF nucleic acid sequence with human M-CSF nucleic acid sequence (VELOCIGENE® Allele Identification Number 5093) in a single targeting step was constructed using VELOCIGENE® technology as described previously (Valenzuela et al. (2003) High-throughput engineering of the mouse genome coupled with high-resolution expression analysis, Nat. Biotechnol. 21:652-659). Mouse and human M-CSF DNA were obtained from bacterial artificial chromosome (BAC) RPCI-23, clone 373B18 and from BAC RPCI-11, clone 101M23 respectively. In brief, a linearized targeting construct generated by gap repair cloning containing mouse M-CSF upstream and downstream homology arms flanking a 17.5 kb human M-CSF sequences extending from exon 2 to 633 nt downstream of non-coding exon 9, and a foxed drug selection cassette was electroporated into RAG2$^{+/-}$ γc$^{Y/-}$ mouse embryonic stem (ES) cells, which was made from a commercially available V17 ES cell line (BALB/c×129 F1). Mouse ES cells carrying a heterozygous deletion of the M-CSF gene were identified by Loss-of-Allele screening with 2 TaqMan qPCR assays that recognized sequences in intron 2 (TUF primer, 5'-CCAG-GAATGTCCACTATGGATTC-3' (SEQ ID NO:13); TUP probe, 5' ACTGCTCCTTGACCCTGCTCTGACTCA-3' (SEQ ID NO:14); TUR primer, 5'-TGGGCTGACTTC-CCAAAGG-3' (SEQ ID NO:15)) and in the 3' flanking sequence (TDF primer, 5'-TTAGGTGCTAGTAGGCTG-GAAAGTG-3' (SEQ ID NO:16); TDP probe, 5'-TG-CAATCGCAGCTTCTCTCCTTACTAGGCT-3 (SEQ ID NO:17)'; TDR primer, 5'-AATAGGAAGAACGAACAG-GTCTAATACC-3' (SEQ ID NO:18)) of the mouse Csf1 gene. Simultaneous replacement of the mouse gene with the human CSF1 gene was confirmed by Gain-of-Allele TaqMan assays that detected one copy of a sequence in intron 2 of CSF1 (forward primer, 5'-GCTGCTTGCCTGGGTTAGTG-3' (SEQ ID NO:19); probe, 5'-TGCCCAGGAACATCAAC-CACTGATTCTG-3' (SEQ ID NO:20); reverse primer, 5'-GAGGGACAGCAGACCTCAGAAG-3' (SEQ ID NO:21)) and one copy of the neomycin resistance (neor) cassette (forward primer, 5'-GGTGGAGAGGCTAT- TCGGC-3' (SEQ ID NO:22); probe, 5'-TGGGCACAACA-GACAATCGGCTG-3' (SEQ ID NO:23); reverse primer, 5'-GAACACGGCGGCATCAG-3' (SEQ ID NO:24); see FIG. 8. The qPCR assay that recognizes the CSF1 sequence does not amplify DNA from the mouse genome. The same assays were used to confirm the genotypes of mice derived from the targeted ES cells. Cre-mediated excision of the drug selection cassette was confirmed with the neor TaqMan assay. All primer-probe sets were supplied by Biosearch Technologies. Probes were labeled with 6-carboxy-fluorecein (FAM) on their 5' ends and BHQ-1 on their 3' ends.

Correctly targeted ES cells were further electroporated with a transient Cre-expressing vector to remove the drug selection cassette. Targeted ES cell clones without drug cassette were introduced into an 8-cell stage mouse embryo by the VELOCIMOUSE® method (Poueymirou et al. (2007)). VELOCIMICE® (F0 mice fully derived from the donor ES cell) bearing the humanized M-CSF gene (VG 5093) were identified by genotyping for loss of mouse allele and gain of human allele using a modification of allele assay (Valenzuela et al. (2003)).

Mouse Maintenance.

Balb/c-Rag2$^{-/-}$ γc$^{-/-}$ M-CSF$^{m/m}$, Balb/c-Rag2$^{-/-}$ γc$^{-/-}$ M-CSF$^{h/m}$ and Balb/c-Rag2$^{-/-}$ γc$^{-/-}$ M-CSF$^{h/h}$ mice were kept under specific pathogen-free conditions in the animal care facility at Yale University. All mouse experiments were approved by the Institutional Animal Care and Use Committee of Yale University.

Making Humanized M-CSF Mice.

To validate whether physiologic expression of human M-CSF in a mouse results in improved differentiation of human macrophages in the humanized mice, the Balb/c Rag2$^{-/-}$ γc$^{-/-}$ mice were engineered to express human M-CSF. The Balb/c strain with Rag2$^{-/-}$ γc$^{-/-}$ deficiency serves as successful model system for the study of the human immune system in mice (Traggiai E et al. (2004) Development of a human adaptive immune system in cord blood cell-transplanted mice, Science 304:104-107). In order to circumvent supra-physiological expression of human M-CSF in these mice, a strategy to replace mouse M-CSF coding sequence with the human counterpart was adopted. A construct (FIG. 8) for replacing, in a single targeting step, the majority of the M-CSF open reading frame with human M-CSF coding sequence (VELOCIGENE® Allele Identification Number 5093), was constructed using the VELOCIGENE® technology as described previously (Valenzuela et al. (2003)). Of note, the promoter and other regulatory elements (such as 5'UTR) of the mouse were preserved in this vector. The linearized targeting vector was electroporated into the Balb/c×129 Rag 2$^{-/-}$ γc$^{-/-}$ embryonic stem cells. Correctly targeted ES cells were further electroporated with a transient Cre-expressing vector to remove the drug selection cassette. Targeted ES cell clones without drug cassette were introduced into an 8-cell stage mouse embryo by the VELOCIMOUSE® method (Poueymirou et al. (2007)). VELOCIMICE® (F0 mice fully derived from the donor ES cell) bearing the humanized M-CSF gene (VG 5093) were identified by genotyping for the loss of the mouse allele and gain of the human allele using a modification of allele assay (Valenzuela et al. (2003)). Through sequential intercrossing of progenies, Balb/c Rag2$^{-/-}$ γc$^{-/-}$ mice chimeric mice and germline transmitted mice with mouse and human M-CSF (M-CSF$^{m/h}$; heterozygous knockin) and human M-CSF only (M-CSF$^{h/h}$; homozygous knockin) were generated.

Characterization of Humanized M-CSF Mice.

Figure 1B:
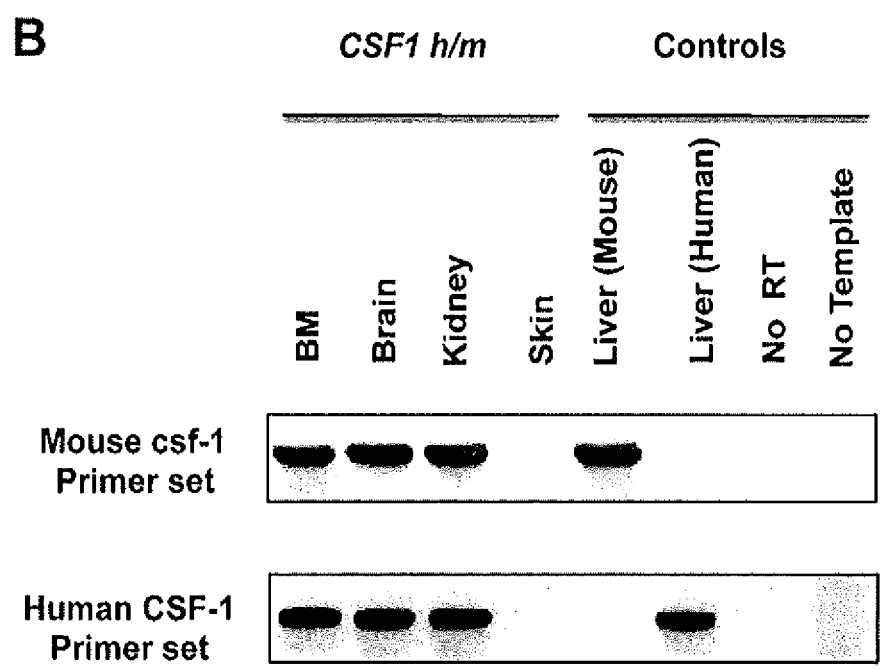
Figures 1C, 1D, 1E:
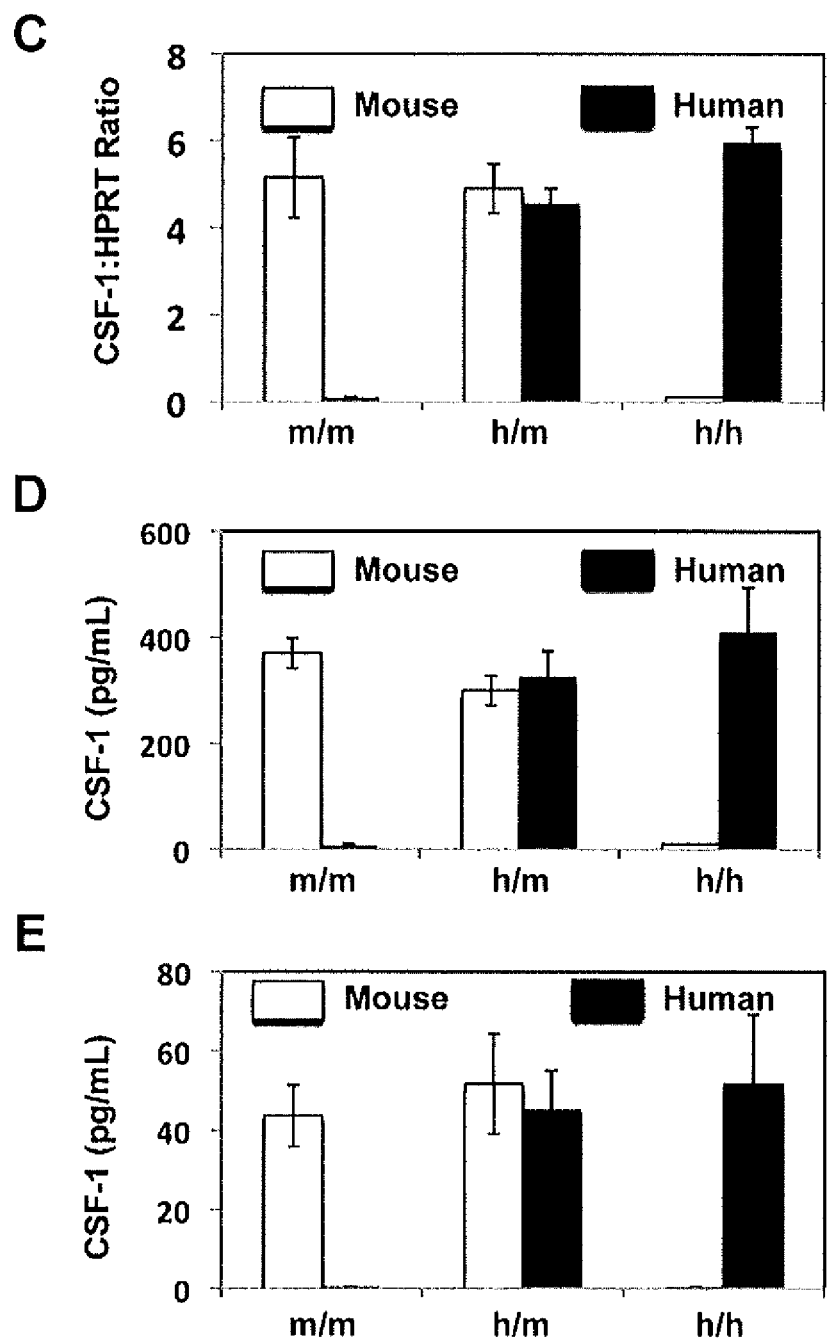

Expression of human M-CSF in the humanized M-CSF mice was evaluated. Organs from either M-CSF$^{m/m}$ or M-CSF$^{h/h}$ mice were harvested and analyzed for murine and human M-CSF mRNA expression using primers that are species specific. As shown in FIGS. 1A and 1B, M-CSF is expressed in the majority of the analyzed organs including BM, spleen, blood, liver, brain, lung, testis and kidney. However, thymus and skin did not show detectable expression of M-CSF. Of note, the expression pattern of mouse and human M-CSF was comparable between M-CSFrn$^{m/m}$ and M-CSF$^{h/h}$ mice, respectively. Next, expression levels of mouse and human M-CSF in M-CSF$^{m/m}$, M-CSF$^{m/h}$, and M-CSF$^{h/h}$ mice were quantified. Bone marrow mesenchymal stromal cells (MSCs) were isolated and the expression levels of M-CSF mRNA were quantified using Realtime-PCR (FIG. 1C) and M-CSF protein (secreted) was quantified using ELISA (FIG. 10). M-CSF$^{m/m}$ mice expressed only mouse M-CSF, M-CSF$^{m/h}$ mice expressed both mouse and human M-CSF and M-CSF$^{h/h}$ mice expressed only human M-CSF. Expression levels of human M-CSF was comparable with mouse M-CSF. In line with these data, analysis of CSF-1 in serum revealed comparable expression levels of CSF-1 protein in m/m, h/m, and h/h mice (FIG. 1E). Hemizygocity does not lead to decreased gene and protein expression levels, indicating that gene-dosage levels seem not to be limiting for this cytokine.

Figure 2A:
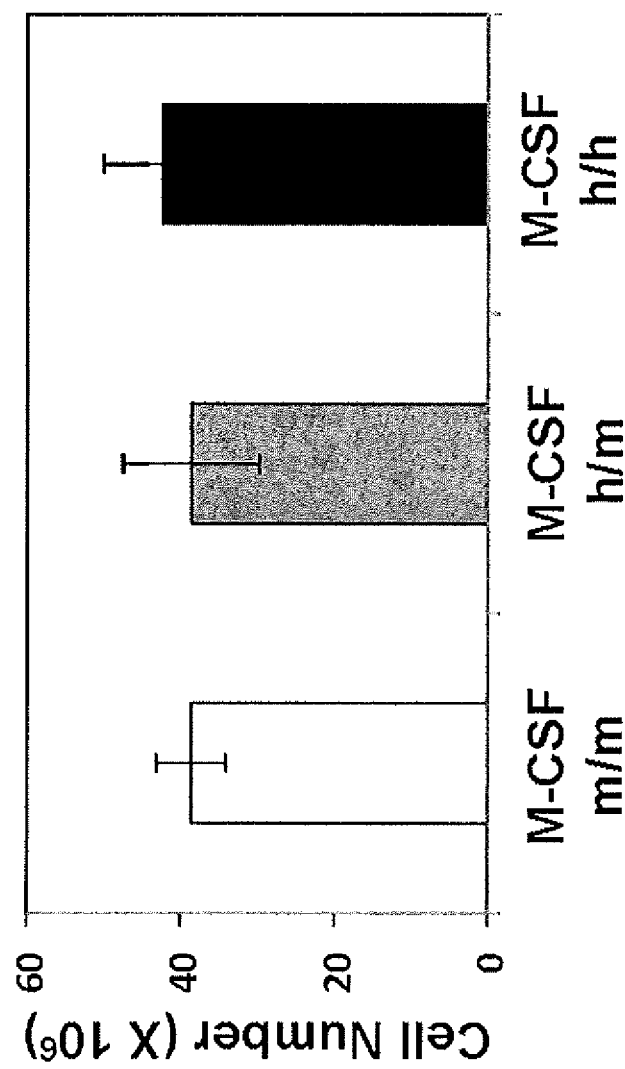
FIG. 2A illustrates absolute numbers of bone marrow (BM) cells of M-CSF$^{m/m}$, M-CSF$^{m/h}$ and M-CSF$^{h/h}$ mice, as average per animal (two tibia and fibula); each group contains n=5 mice, age 4 weeks; error bars indicate±SEM; data are representative of 3 independent experiments.
Figure 2B:
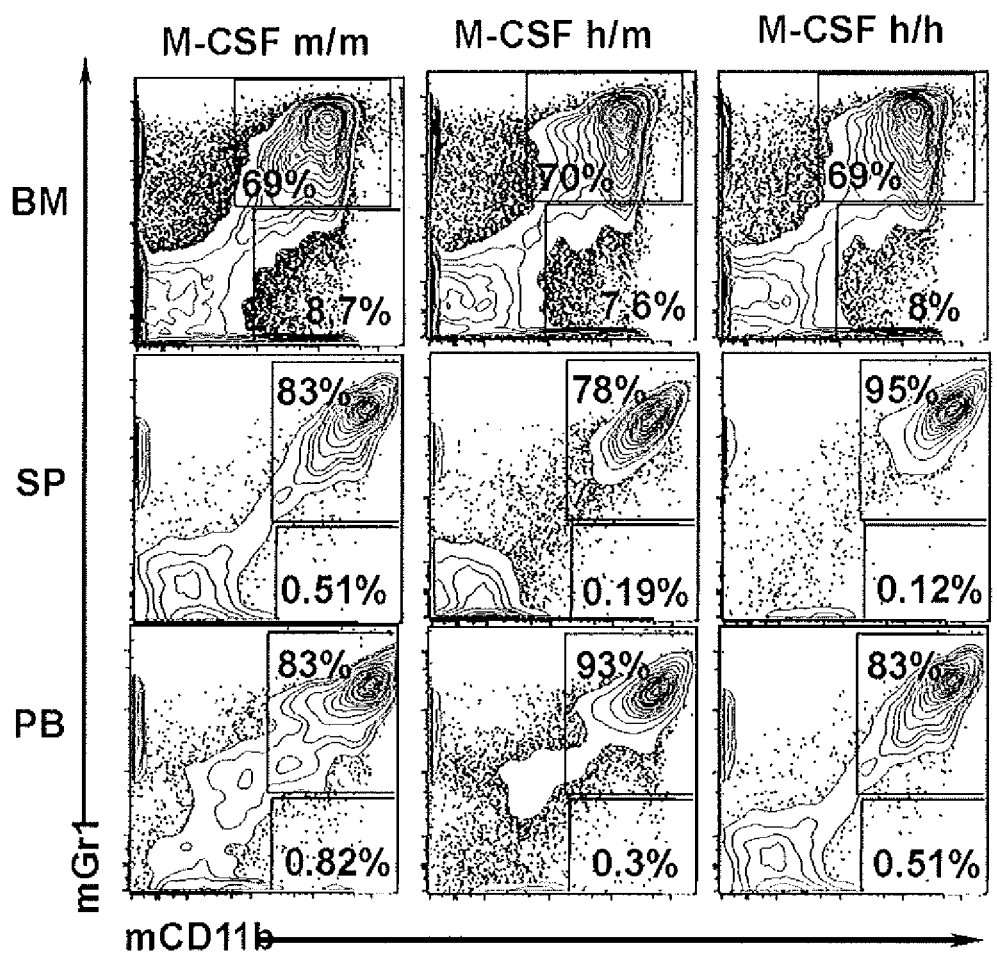
FIG. 2B illustrates flow cytometry analysis of a stained single cell suspension of BM (top), Spleen (middle) and Peripheral Blood (PB) from M-CSF$^{m/m}$, M-CSF$^{m/h}$ and M-CSF$^{h/h}$ mice; stained with Gr1 and CD11b antibodies.
Figure 2C:
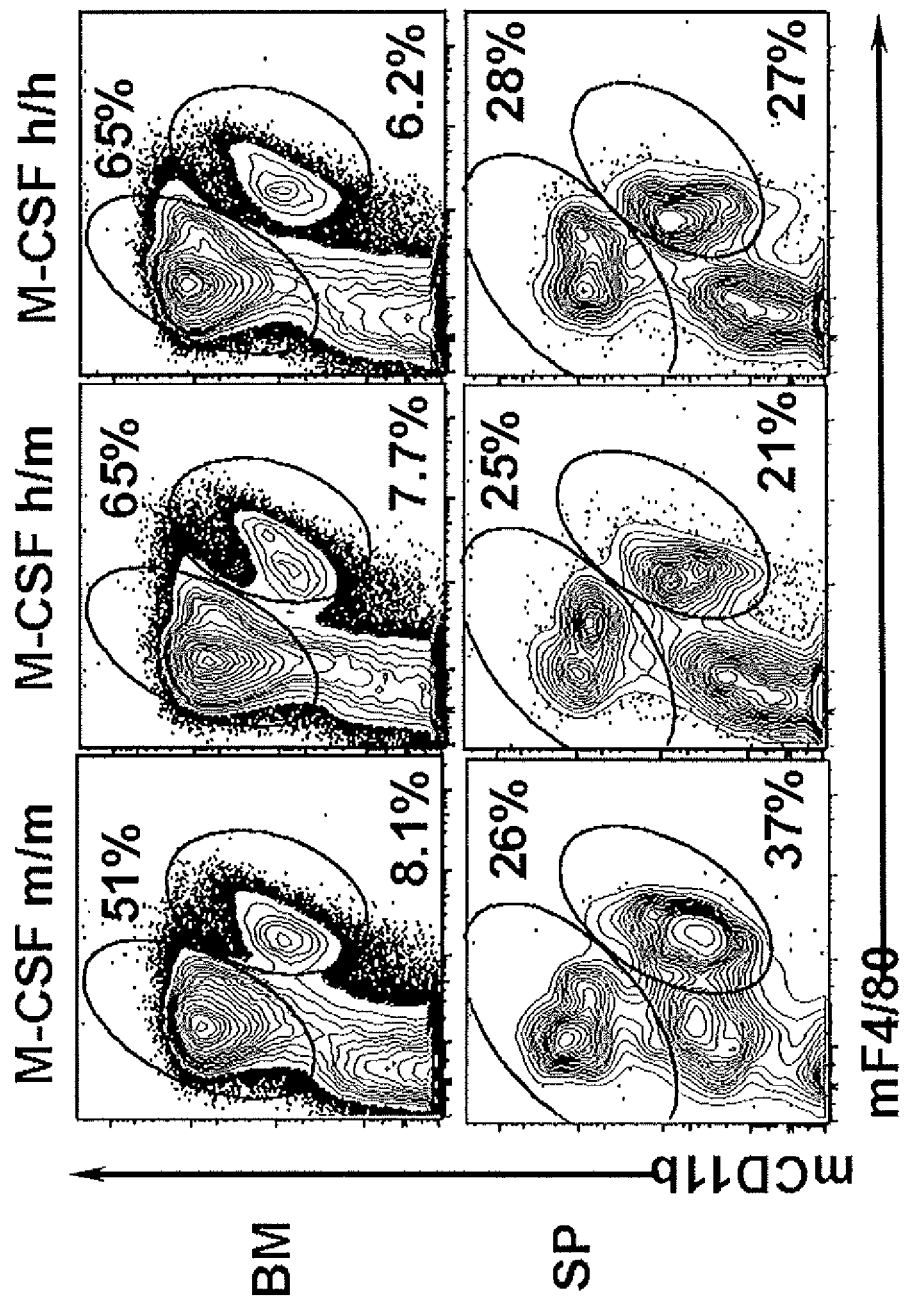
FIG. 2C illustrates flow cytometry analysis of a stained single cell suspension of BM (top) and Spleen (middle) from M-CSF$^{m/m}$, M-CSF$^{m/h}$ and M-CSF$^{h/h}$ mice; stained with F4/80 and CD11b antibodies.
Figure 9:
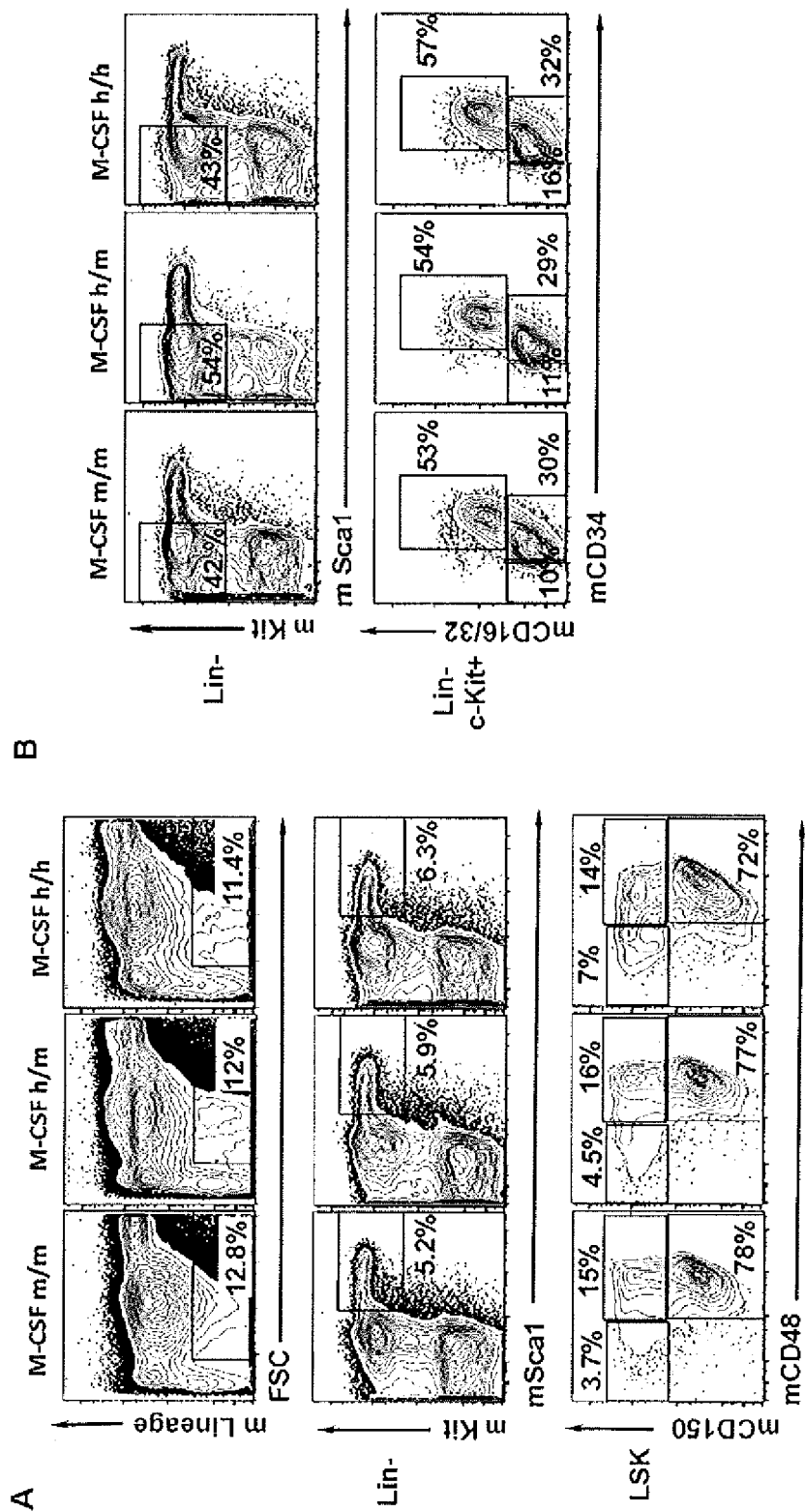
FIG. 9A,B illustrates the frequencies of the HSC compartment and myeloid progenitor compartment in M-CSF$^{m/m}$, M-CSF$^{h/m}$, and M-CSF$^{h/h}$ mice. BM cells from M-CSF$^{m/m}$, M-CSF$^{m/h}$ and M-CSF$^{h/h}$ mice were stained with lineage, c-Kit, Sca1, CD150, CD48, CD16/32, and CD34 antibodies, and analyzed by flow cytometry. (A) Lineage$^-$ cells (top) were gated and discriminated based on Sca1 and c-Kit expression (middle). Lineage$^-$Sca1$^+$c-Kit$^+$ (LSK) cells were gated and further discriminated based on CD150 and CD48 expression (bottom). (B) Lineage$^-$ cells were pre-gated and discriminated based on Sca1 and c-Kit expression (top). Lineage$^-$ c-Kit$^+$Sca1$^-$ cells were gated and further discriminated based on CD16/32 and CD34 expression (bottom).

To investigate whether replacing mouse M-CSF with human M-CSF results in deleterious effects, especially on the bone and hematopoiesis, M-CSF$^{h/h}$ mice were analyzed at various ages. Earlier studies have documented that mice with defective M-CSF signaling (Csf1$^{op/op}$ and Csf1r$^{-/-}$) exhibit tooth eruption failure and bone defects (Dai, X. M. et al. (2002) Targeted disruption of the mouse colony-stimulating factor 1 receptor gene results in osteopetrosis, mononuclear phagocyte deficiency, increased primitive progenitor cell frequencies, and reproductive defects, Blood 99:111-120; Felix, R. et al. (1990) Macrophage colony stimulating factor restores in vivo bone resorption in the op/op osteopetrotic mouse, Endocrinology 127:2592-2594; Wiktor-Jedrzejczak, W. et al. (1990) Total absence of colony-stimulating factor 1 in the macrophage-deficient osteopetrotic (op/op) mouse, Proc. Natl. Acad. Sci. USA 87:4828-4832; Yoshida, H. et al. (1990) The murine mutation osteopetrosis is in the coding region of the macrophage colony stimulating factor gene, Nature 345:442-444). In contrast, M-CSF$^{h/h}$ mice revealed normal teeth and bone properties. Further, unlike the Csf1$^{op/op}$ and Csd1r$^{-/-}$ mice, the total cell content of the BM (FIG. 2A), frequencies of myeloid cells in the BM, spleen (SP) and peripheral blood (PB) (FIG. 2B) and the frequencies of macrophages in the BM and SP (FIG. 2C) were comparable among the M-CSF$^{m/m}$, M-CSF$^{h/m}$ and M-CSF$^{h/h}$ mice. In line with this observation, the frequencies of the HSC compartment (including long term-HSC, short term-HSCs and multipotent progenitors) and myeloid progenitor compartment (including common myeloid progenitors, granulocyte monocyte progenitor and megakaryocyte erythrocyte progenitors) were comparable among the M-CSF$^{m/m}$, M-CSF$^{h/m}$ and M-CSF$^{h/h}$ mice (FIG. 9).

Figure 2D:
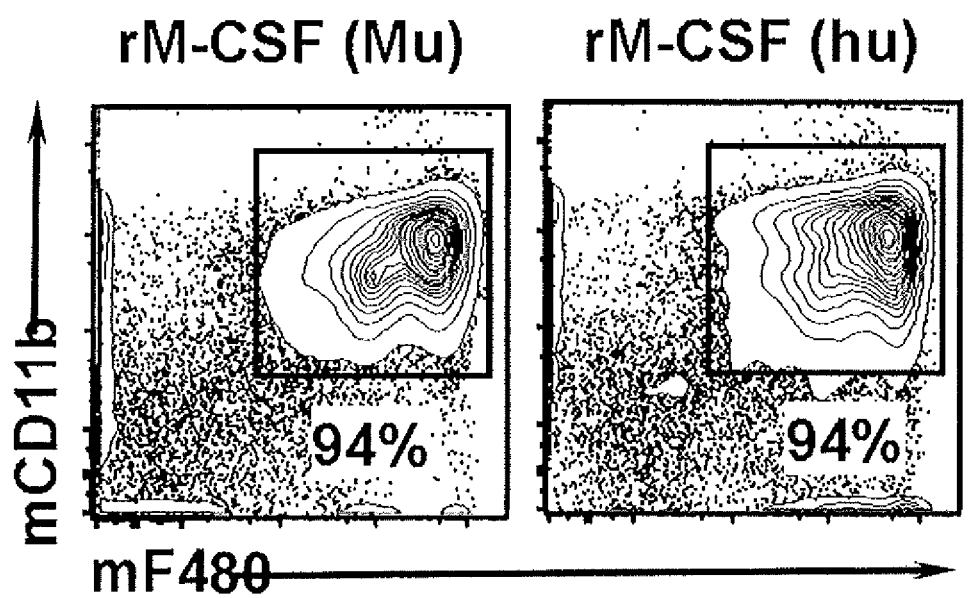
FIG. 2D illustrates flow cytometry analysis of BM cells that were isolated and cultured either in the presence of recombinant mouse M-CSF (left) or human M-CSF (right) for 7 days; cells were stained with F4/80 and CD11b antibodies.
Figure 2E:
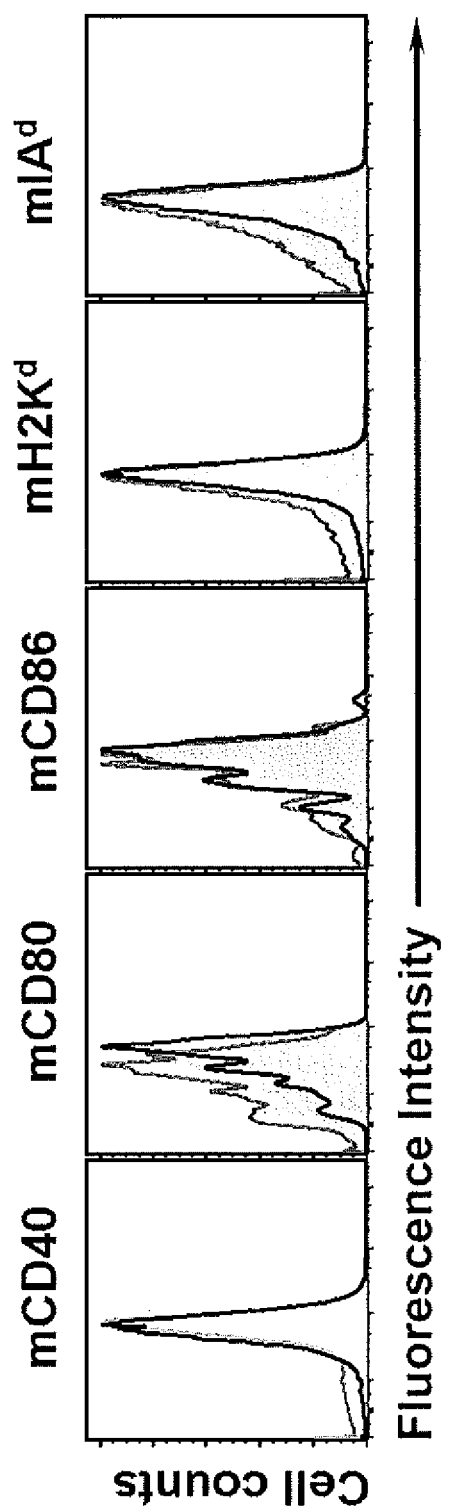
FIG. 2E illustrates flow cytometry analysis of BM cells that were isolated and cultured either in the presence of recombinant mouse M-CSF (filled) or human M-CSF (open) for 7 days; cells were stained with indicated surface markers.

A possible explanation for the normal hematopoiesis and bone development in the M-CSF$^{h/h}$ mice might be that human M-CSF is cross reactive with mouse cells. To validate this, total BM cells from M-CSF$^{m/m}$ were isolated and cultured in the presence of either recombinant murine M-CSF or recombinant human M-CSF. Whereas BM cells cultured in the absence of cytokine failed to survive, cells cultured in the presence of either human or mouse M-CSF showed comparable levels of in vitro differentiation (FIG. 2D). Analysis of these in vitro differentiated macrophages for the expression of co-stimulatory molecules and MHC indicated comparable levels of these molecules in the presence of either human or mouse M-CSF (FIG. 2E). Consistent with our findings, previous studies documented that human M-CSF is active in mouse target cells, whereas mouse M-CSF is not cross-reactive with human cells (Sieff, C. A. (1987) Hematopoietic growth factors, J. Clin. Invest. 79:1549-1557).

Example 3

Differentiation of Human Monocytes/Macrophages in Humanized M-CSF Mice

Figure 3A:
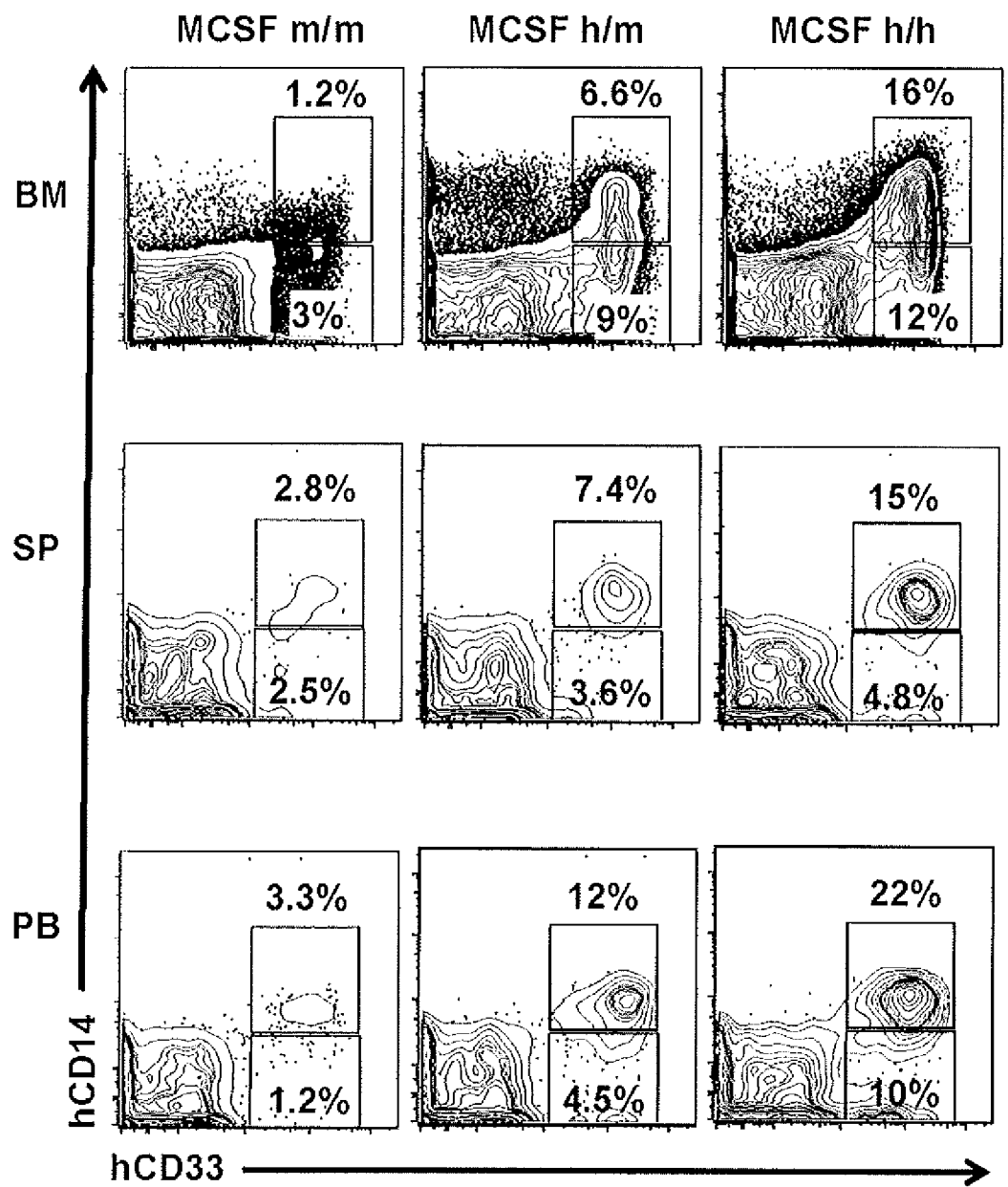
FIG. 3A illustrates flow cytometry of single cell suspensions of BM (top), Spleen (middle) and Peripheral Blood (PB) from human CD34$^+$ cells engrafted in M-CSF$^{m/m}$, M-CSFm$^{m/h}$ and M-CSF$^{h/h}$ mice; staining is with CD45, CD14 and CD33 human antibodies; cells that are human CD45$^+$ were pre-gated and discriminated based on CD14 and CD33 expression.
Figure 3B:
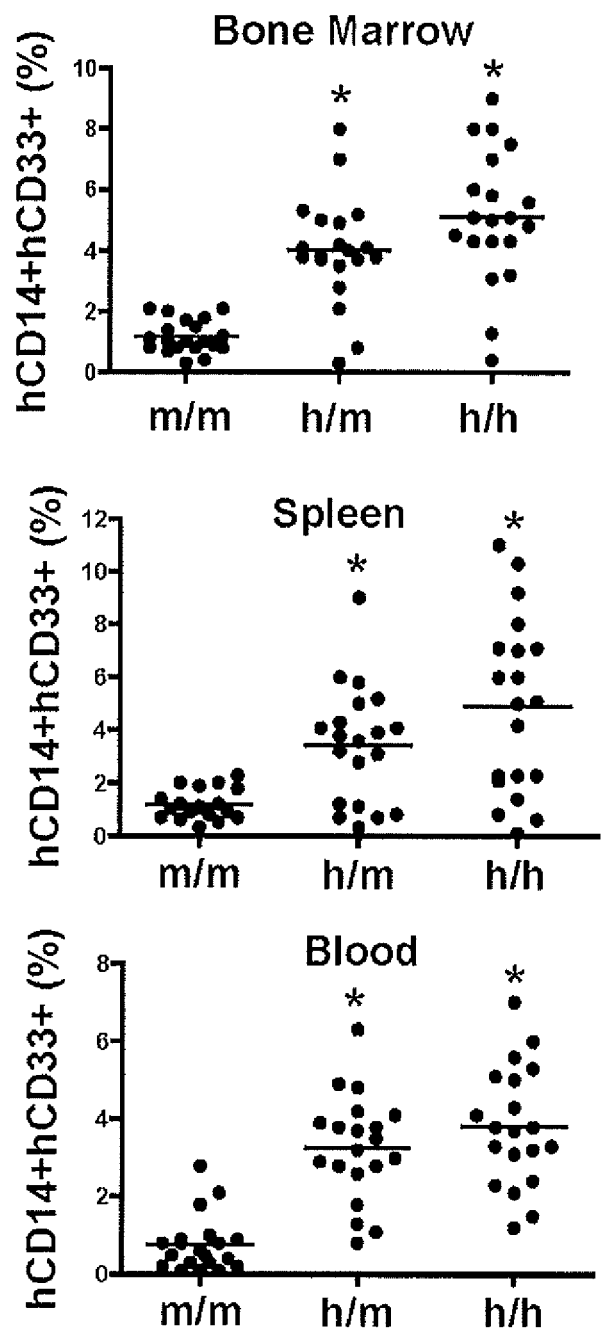
FIG. 3B illustrates relative frequencies of human CD45$_+$ CD14$_+$CD33$_+$ cells of BM (top), spleen (middle) and peripheral blood (PB); absolute numbers of BM cells were determined as average per animal (two tibia and fibula) and of peripheral blood were determined per mL volume of blood; each group contains n=20 mice; each symbol represents an individual mouse, horizontal bars indicate the mean values; data are representative of 5 independent experiments.
Figure 3C:
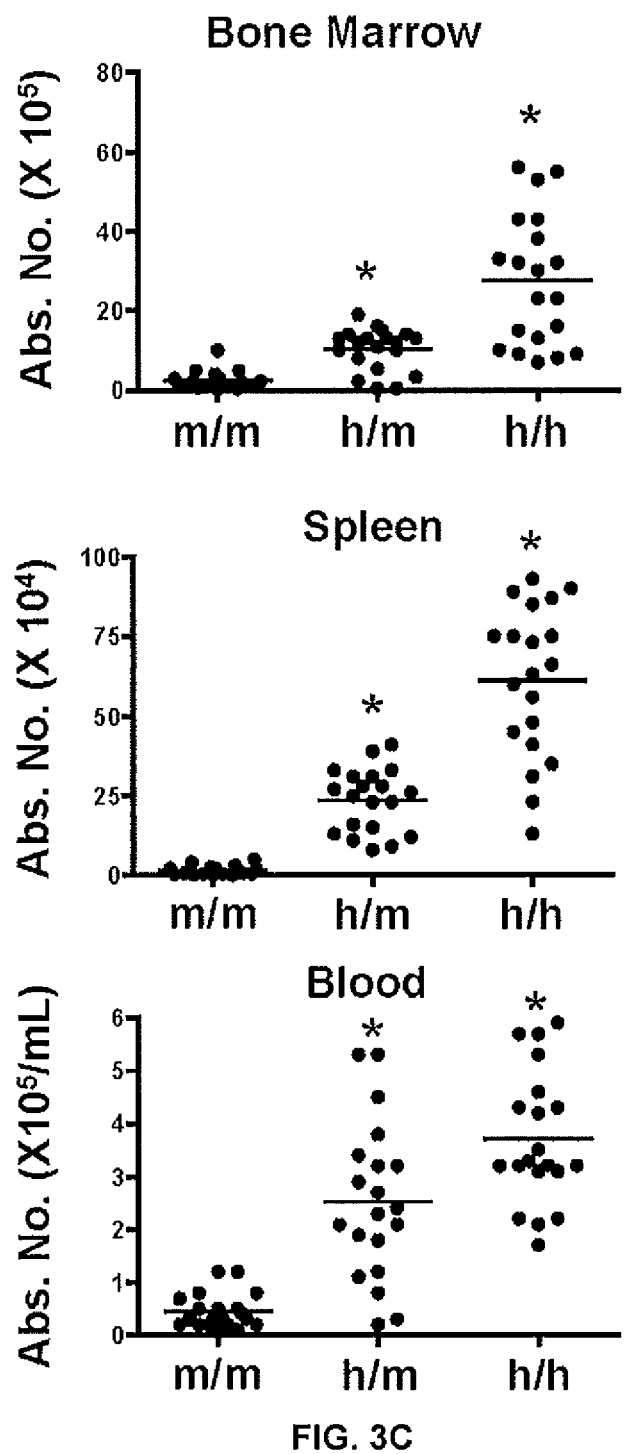
FIG. 3C illustrates absolute frequencies of human CD45$_+$ CD14$_+$CD33$_+$ cells of BM (top), spleen (middle) and peripheral blood (PB); absolute numbers of BM cells were determined as average per animal (two tibia and fibula) and of peripheral blood were determined per mL volume of blood; each group contains n=20 mice; each symbol represents an individual mouse, horizontal bars indicate the mean values; data are representative of 5 independent experiments.

To evaluate the impact of M-CSF humanization, sub-lethally irradiated newborn Rag2$^{-/-}$ γc$^{-/-}$ M-CSF$^{m/m}$, Rag2$^{-/-}$ γc$^{-/-}$ M-CSF$^{h/m}$ and Rag2$^{-/-}$ γc$^{-/-}$ M-CSF$^{h/h}$ pups were transplanted intra-hepatically (i.h) with ~2×10$^5$ purified human fetal liver CD34$^+$ cells. Recipients were then bled at 8 weeks after transplantation to confirm the cells of donor (based on human CD45 expression) origin. Twelve weeks after transplantation, recipients were sacrificed and their BM, SP and PB were harvested. Analysis revealed augmentation of the relative and absolute frequencies of CD14$^+$CD33$^+$ monocyte/macrophage lineage cells in the BM, SP and PB of both M-CSF$^{h/m}$ and M-CSF$^{h/h}$ mice as compared with M-CSF$^{m/m}$ mice (FIG. 3A-C). Although M-CSF$^{h/m}$ mice exhibited increased frequencies of CD14$^+$CD33$^+$ cells, the maximum frequencies of CD14$^+$CD33$^+$ cells were found in the M-CSF$^{h/h}$ mice. Interestingly, in addition to this increase, the frequencies of CD14$^-$CD33$^+$ cells were also increased in the BM, SP and PB of M-CSF$^{h/m}$ and M-CSF$^{h/h}$ mice (FIG. 3A).

Figure 4A:
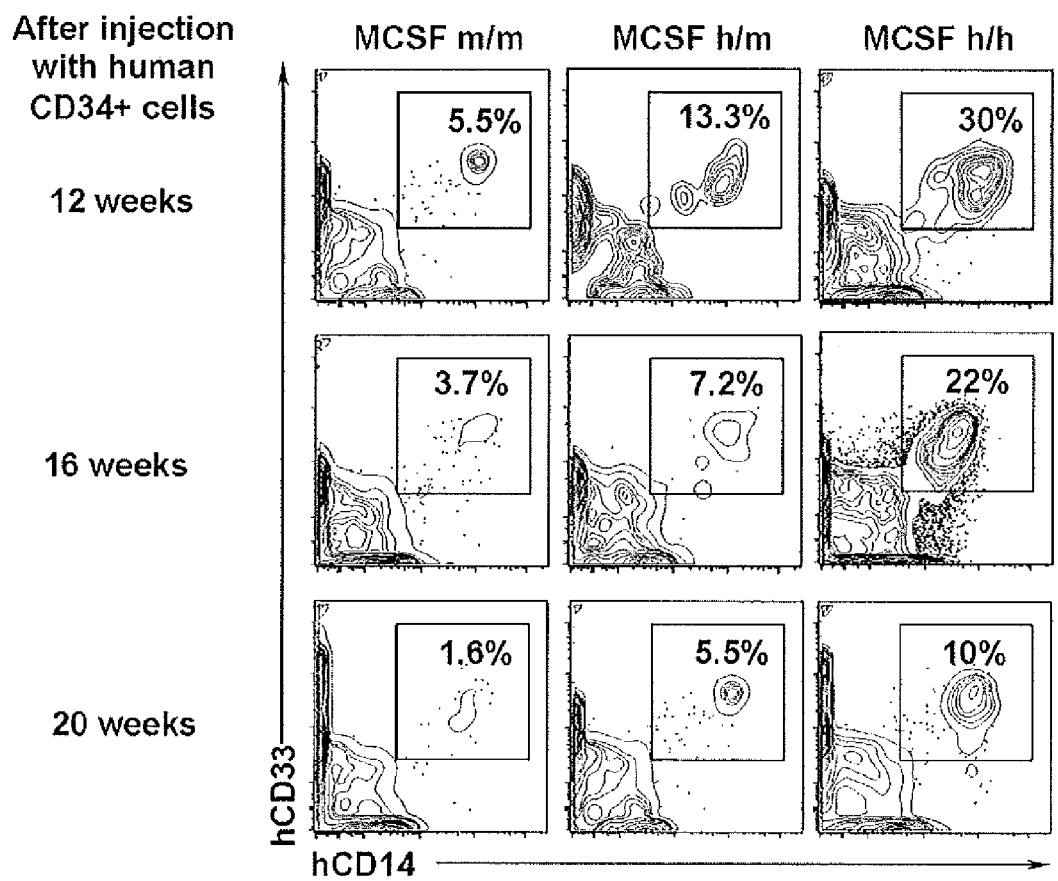
FIG. 4A illustrates flow cytometry analysis of stained cells from human CD34$^+$ cells engrafted M-CSF$^{m/m}$, M-CSF$^{m/m}$ and M-CSF$^{h/h}$ mice bled after 12, 16 and 20 weeks of transplantation; cells were stained with CD45, CD14 and CD33 human antibodies; cells that are human CD45$^+$ were pre-gated and discriminated based on CD14 and CD33 expression.
Figure 4B:
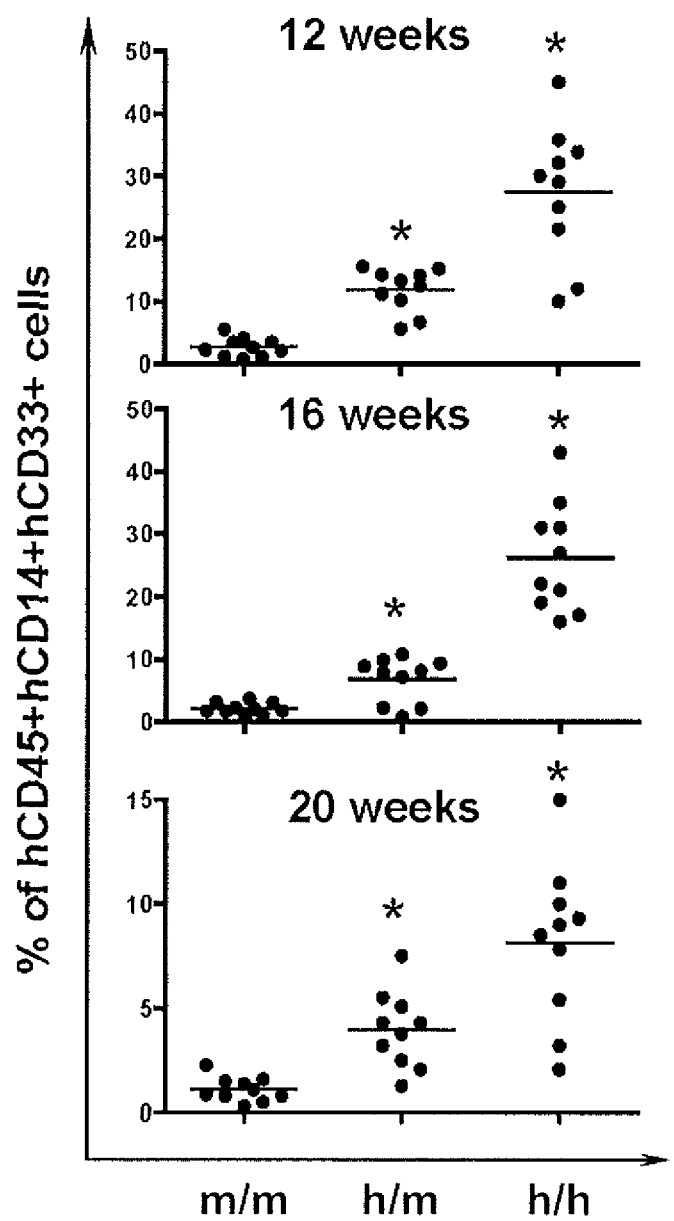
FIG. 4B illustrates relative frequencies of human CD45$^+$ CD14$^+$CD33$^+$ cells; each group contains n=10 mice; each symbol represents an individual mouse, horizontal bars indicate the mean values; data are representative of 3 independent experiments.

To analyze whether the human M-CSF knockin mice support sustained human myelopoiesis, recipients were analyzed at 12, 16 and 20 weeks after transplantation. While human CD14$^+$CD33$^+$ monocyte/macrophage lineage cells were slightly reduced at 16 weeks and highly reduced after 20 weeks of transplantation in the M-CSF$^{m/m}$ mice, significant proportions of human CD14$^+$CD33$^+$ cells were observed in both M-CSF$^{h/m}$ and M-CSF$^{h/h}$ mice at even 16 and 20 weeks. Nevertheless, the maximum frequencies of human CD14$^+$CD33$^+$ cells were seen in the M-CSF$^{h/h}$ mice (FIGS. 4A and 4B).

Figure 5:
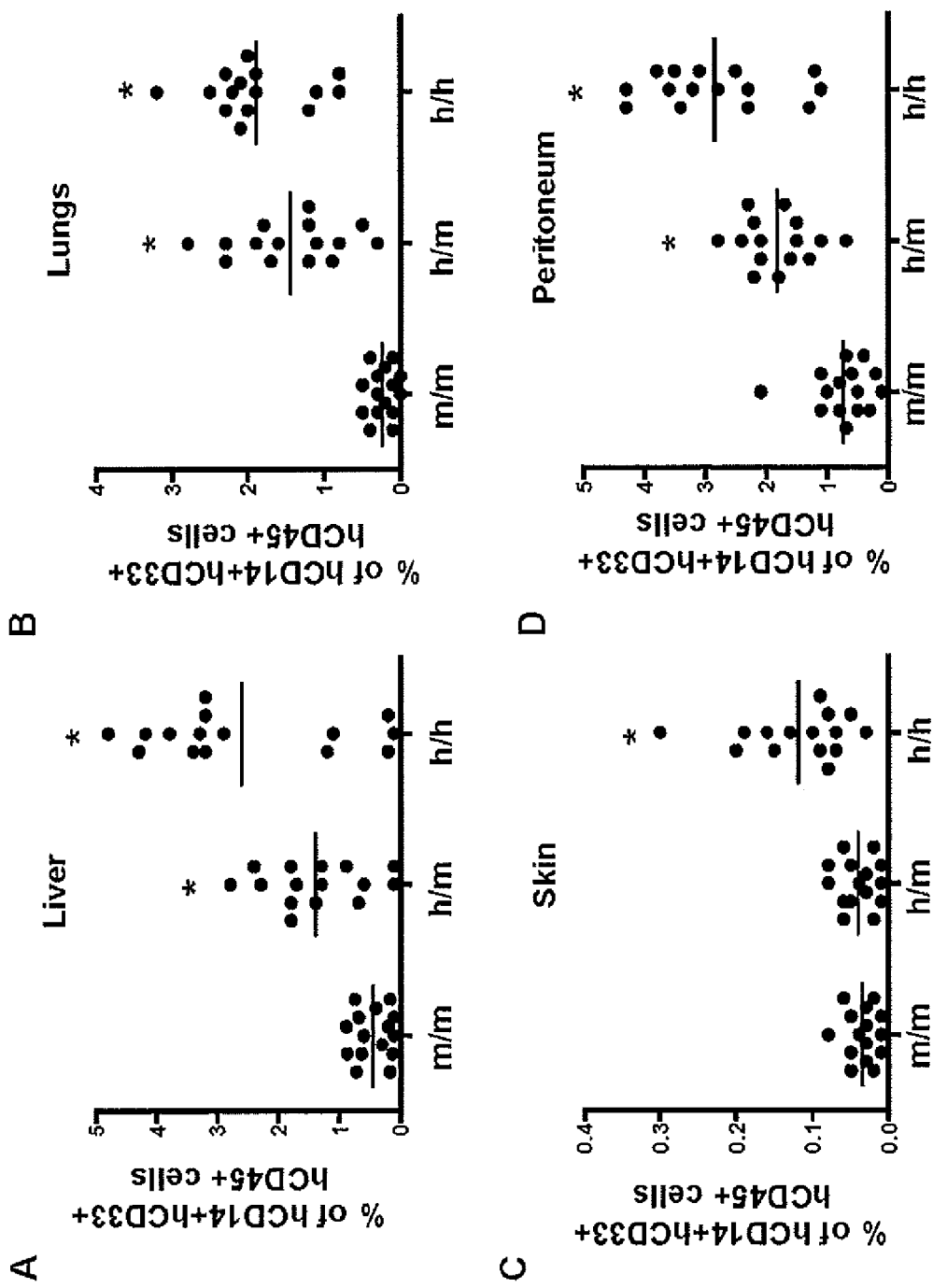
FIG. 5 illustrates analysis of flow cytometry results from M-CSF$^{m/m}$, M-CSF$^{m/h}$ and M-CSF$^{h/h}$ mice engrafted with human CD34$^+$ cells and 12 weeks after transplantation, when mice were sacrificed and perfused with PBS; Liver (A), Lungs (B) and Skin (C) were harvested and single cell suspensions were prepared; peritoneal cavity cells (D) were collected by aspirating with PBS; cells were stained with human CD45, CD14 and CD33 antibodies, and analyzed by flow cytometry; each symbol represents an individual mouse, horizontal bars indicate the mean values; data are representative of 3 independent experiments.

Next, whether the humanized M-CSF mice support efficient differentiation of human tissue macrophages was assessed. To this end, M-CSF$^{m/m}$, M-CSF$^{m/h}$ and M-CSF$^{h/h}$ mice were perfused with PBS and their organs (including liver, lungs and skin) were harvested. Cells of the peritoneum were obtained by flushing the peritoneal cavity with PBS. Single cell suspensions were prepared and the frequencies of human CD14$^+$CD33$^+$ cells were calculated. As expected, the frequencies of human CD14$^+$CD33$^+$ cells were significantly increased in the liver, lungs and peritoneum of both M-CSF$^{m/h}$ and M-CSF$^{h/h}$ mice. However, analysis of skin explants revealed comparable frequencies of human CD14$^+$CD33$^+$ cells between M-CSF$^{m/m}$ and M-CSF$^{m/h}$ mice, although a significant increase of these cells was observed in the skin explants of M-CSF$^{h/h}$ mice (FIG. 5). Taken together, these data suggest that expression of human M-CSF in mice improves myeloid/macrophage lineage differentiation of human HSCs.

Example 4

Human Monocyte/Macrophage Function in Humanized M-CSF Mice

Figures 6A, 6B:
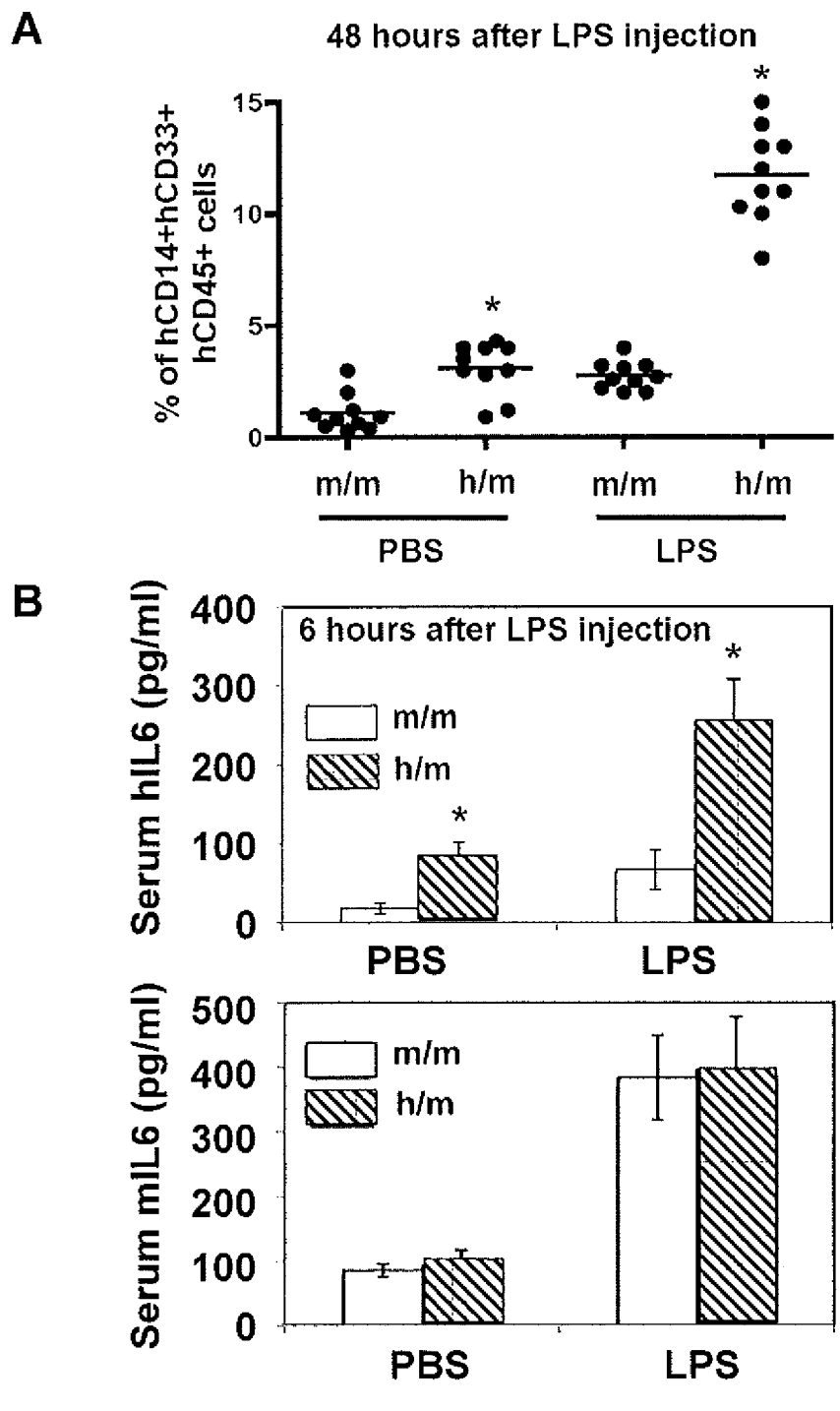
FIG. 6 illustrates results of LPS stimulation. (A) M-CSF$^{m/m}$ and M-CSF$^{m/h}$ mice were engrafted with human CD34$^+$ cells and 12 weeks after transplantation, LPS was injected i.p. and 48 hours later mice were sacrificed and the frequencies of human CD45$^+$CD14$^+$CD33$^+$ cells in the spleen were determined; PBS-injected mice served as controls; each symbol represents an individual mouse, horizontal bars indicate mean values. (B), (C) M-CSF$^{m/m}$ and M-CSF$^{m/h}$ mice were engrafted with human CD34$^+$ cells and 12 weeks after transplantation, LPS was injected i.p. Six hours later, mice were bled and the serum levels of human (right) and mouse (left) IL-6 and TNFα were quantified by ELISA; PBS-injected mice served as controls; mean values of triplicate samples are shown; error bars indicate±SEM.

To investigate whether the human CD14$^+$CD33$^+$ monocytes/macrophages in the humanized M-CSF mice functioned normally, both in vivo and in vitro functional studies were performed. Sublethally irradiated M-CSF$^{m/m}$ and M-CSF$^{m/h}$ pups were injected with fetal liver CD34$_+$ cells and 12 weeks after transplantation, donor derived hematopoiesis was assessed and recipient mice were injected with either LPS or PBS. Two days after LPS injection, recipients were analyzed for the frequencies of human CD14$^+$CD33$^+$ cells in the spleen. While LPS injection induced only a modest increase of monocyte/macrophage lineage cells in the M-CSF$^{m/m}$ mice, when compared with the PBS injected groups, LPS injected M-CSF$^{m/h}$ mice showed a several fold increase of human CD14$^+$CD33$^+$ cells in the spleen (FIG. 6A). Next, the abilities of these cells to produce pro-inflammatory cytokines in response to LPS stimulation in vivo were examined.

Figure 6C:
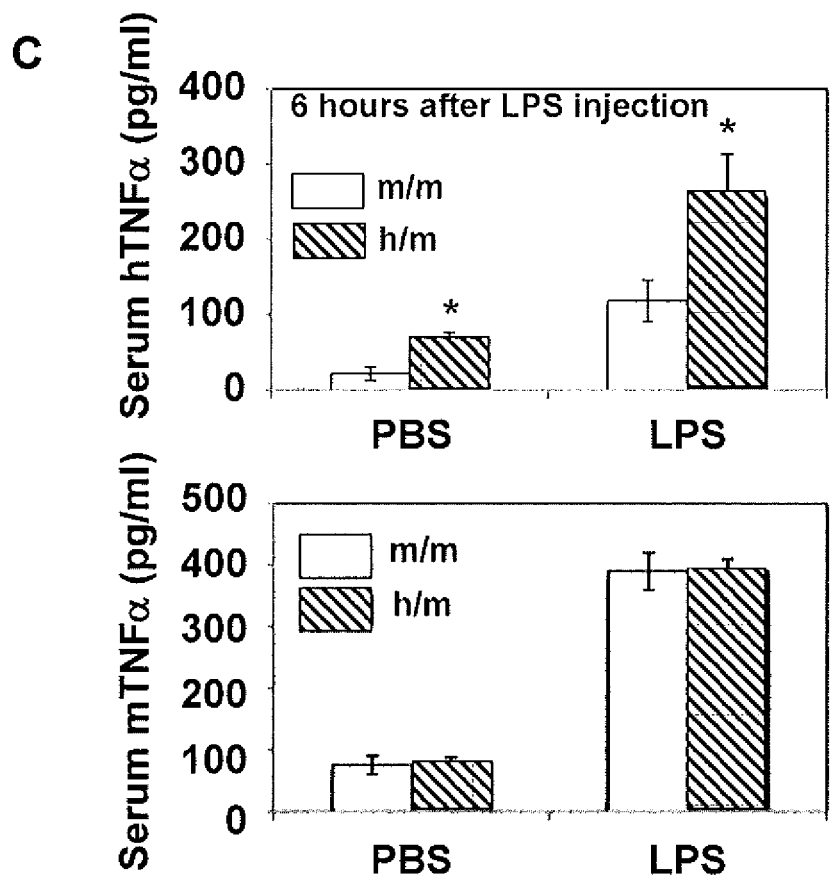
Figure 7C:
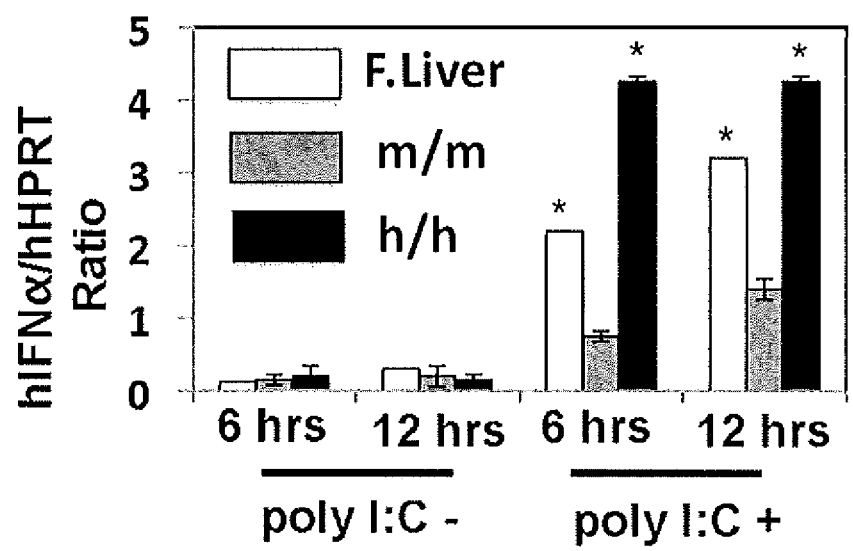
FIG. 7C illustrates levels of interferon-α and -β mRNA in response to poly I:C stimulation. Human CD45$^+$CD14$^+$CD33$^+$ cells were stimulated poly I:C for either 6 or 12 hours and IFNα (left) and IFNβ (right) mRNA levels were quantified by real time PCR; mean values of duplicate samples are shown; error bars indicate±SEM.
Figure 7C:
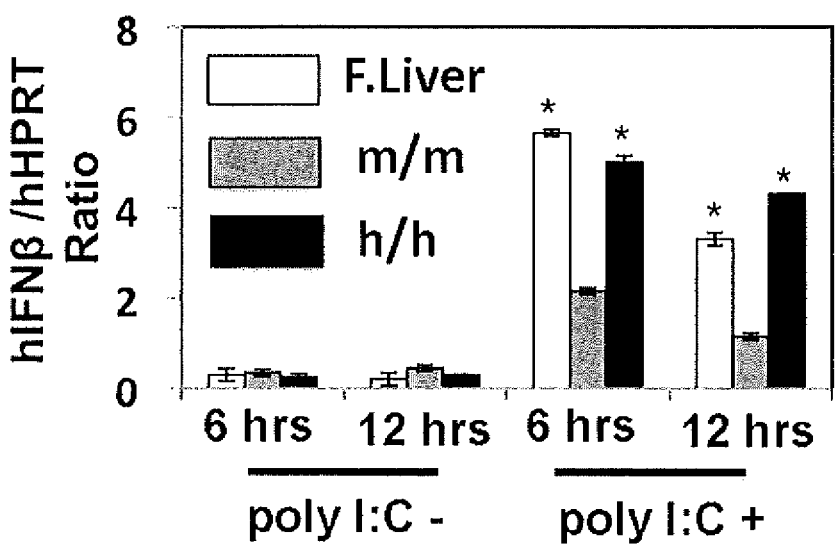
Figure 7D:
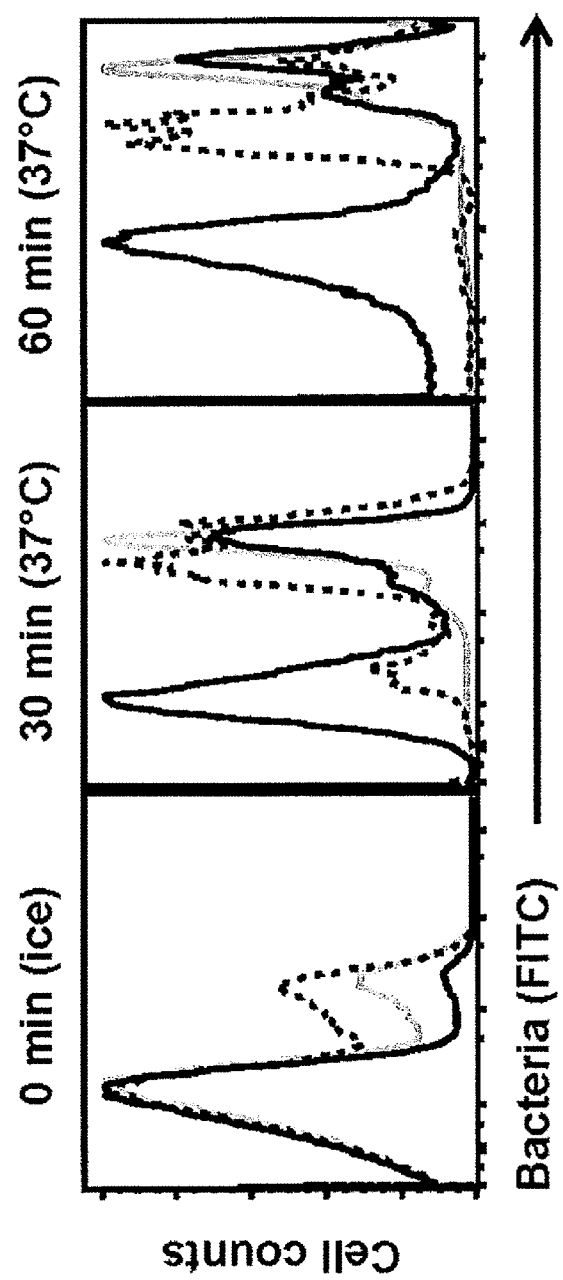
FIG. 7D illustrates phagocytosis, migration, and activation properties of cells from engrafted mice. Human CD45$^+$CD14$^+$CD33$^+$ cells were isolated from humanized mice and incubated with FITC-labeled bacteria at 37° C. either for 30 or 60 minutes and measured by flow cytometry; cells incubated with FITC-labeled bacteria on ice served as controls. Open histograms represent cells from M-CSF$^{m/m}$ mice, dotted histograms represent cells from M-CSF$^{h/h}$ mice, and filled histograms represent cells from human fetal liver.
Figure 7E:
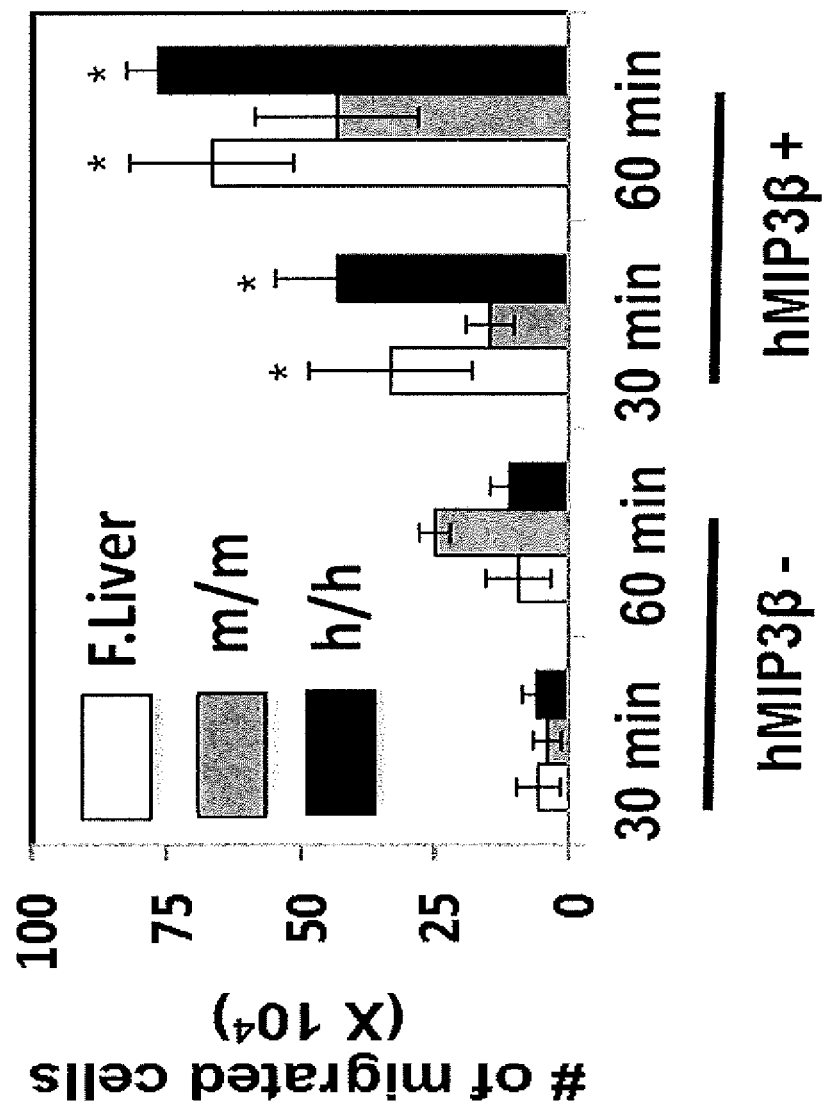
FIG. 7E illustrates chemotaxis of cells in response to MIP3β. Human CD45$^+$CD14$^+$CD33$^+$ cells isolated from M-CSF$^{m/m}$ mice, M-CSF$^{h/h}$, mice and human fetal liver were kept in upper wells and medium containing MIP3β was added in to lower wells; cells were incubated for either 30 or 60 minutes and the number of cells that migrated from upper wells to lower wells was calculated and plotted; mean values of duplicate samples are shown; error bars indicate±SEM.
Figure 7F:
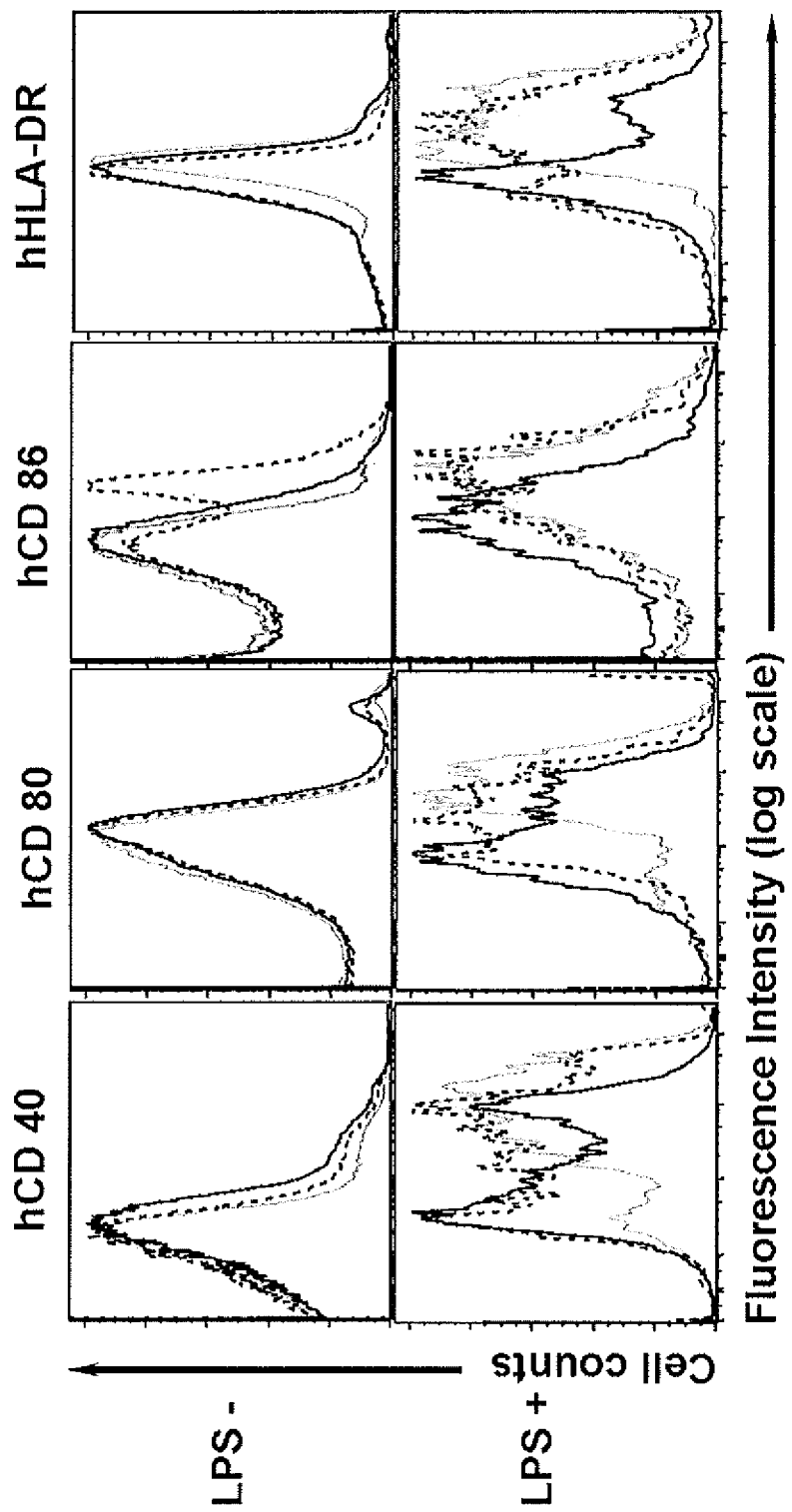
FIG. 7F illustrates enhanced activation of human monocytes/macrophages from engrafted mice based on up-regulation of hCD40, hCD80, hCD86, and hHLA-DR following in vitro LPS stimulation. Human CD45$^+$CD14$^+$CD33$^+$ cells isolated from M-CSF$^{m/m}$ mice, M-CSF$^{h/h}$ mice, and human fetal liver were cultured either in the presence or in the absence of LPS; after 24 hours of stimulation, cells were stained with indicated surface markers and measured by flow cytometry. Open histograms represent cells from M-CSF$^{m/m}$ mice, dotted histograms represent cells from M-CSF$^{h/h}$ mice, and filled histograms represent cells from human fetal liver.

M-CSF$^{m/m}$ and M-CSF$^{m/h}$ mice engrafted with human CD34$_+$ cells were injected with LPS. Six hours after injection, mice were bled and the serum levels of human and mouse IL6 and TNFα were determined by ELISA. Consistent with the increased frequencies of monocytes/macrophages in the humanized M-CSF mice, elevated levels of human IL6 and TNFα were detected in the M-CSF$^{m/h}$ mice. Although the basal levels of these cytokines were higher in the M-CSF$^{m/h}$ mice, LPS stimulation resulted in augmented levels of human IL6 and TNFα in the serum (FIGS. 6B and 6C). Next, the capacity of monocytes/macrophages (obtained from humanized M-CSF mice) to secrete pro-inflammatory cytokines in vitro was analyzed. Human CD14$^+$CD33$^+$ cells were isolated from the spleens of either M-CSF$^{m/m}$ or M-CSF$^{h/h}$ mice, after 12 weeks of reconstitution with human CD34$^+$ cells, and stimulated with LPS in vitro for either 24 or 48 hours. The levels of IL-6 and TNFα cytokines in the cell culture supernatants were assessed by ELISA. In line with the in vivo data, CD14$^+$CD33$^+$ cells purified from M-CSF$^{h/h}$ mice secreted augmented levels of these cytokines in response to LPS (FIGS. 7A and 7B). Similarly, human CD14$^+$CD33$^+$ cells isolated from the humanized M-CSF mice expressed augmented levels of interferon-α and interferon-β mRNA in response to poly I:C stimulation (FIG. 7C). Finally, the phagocytosis, migration and activation properties of human monocytes/macrophages obtained from the humanized M-CSF mice were analyzed. Human CD14$^+$CD33$^+$ cells purified from human CD34$^+$ reconstituted, M-CSF$^{h/h}$ mice exhibited increased phagocytic properties (FIG. 7D) and displayed augmented chemotaxis in response to the chemokine Mip3β (FIG. 7E). As expected, human monocytes/macrophages obtained from the M-CSF$^{h/h}$ mice displayed enhanced activation properties as assessed based on upregulation of co-stimulatory molecules including CD40, CD80 and CD86, and HLA-DR in response to LPS stimulation in-vitro (FIG. 7F). Overall, human monocytes/macrophages differentiated in the presence of human M-CSF in the humanized mice exhibit augmented functional properties.

Generating a mouse with a completely reconstituted and functional hematopoietic/immune system of human origin has been a great challenge in the field. To date, 3 mouse strains (NOD-scid γc$^{-/-}$, [NSG], NOD/Shi-scid γc$^{-/-}$ [NOG], and Balb/c-Rag2$^{-/-}$ γc$^{-/-}$) have been developed. Despite the advantages conferred by each of these strains, human hematopoiesis is incomplete in these mice.

To overcome this major technical challenge, the mouse CSF-1 gene was replaced with its human counterpart. This resulted in efficient human macrophage differentiation in mice that were reconstituted with human hematopoietic stem and progenitor cells. Analysis of the humanized CSF-1 mice indicated efficient differentiation of human monocytes/macrophages in the BM, spleen and peripheral blood. Moreover, human macrophages were detected in several different tissues including, lungs and liver, in these mice, indicating that the presence of CSF-1 in humanized mice is sufficient to promote the differentiation of human tissue macrophages. Additionally, functional studies described herein involving the human monocytes/macrophages, isolated from the CSF1$^{m/m}$ and the CSF1$^{h/h}$ mice indicate that cells from the CSF1$^{h/h}$ mice were better in performing functions such as phagocytosis, migration, activation and cytokine secretion. Based on these findings, it may be inferred that monocytes/macrophages that differentiate in the presence of human CSF-1 function better.

VELOCIGENE® genetic engineering technology was used to generate a novel line of Balb/c-Rag2$^{-/-}$ γc$^{-/-}$ mice that express human CSF-1. Accordingly, the mouse CSF-1 coding region was replaced with the human counterpart without disturbing the regulatory elements, such as the promoter, of the mouse csf1 gene. This resulted in a chimeric gene that contained the mouse regulatory elements and the human CSF-1 coding region. Expression studies of these mice indicated that this chimeric gene is expressed faithfully in both a qualitative and quantitative manner.

The role of CSF-1 in the differentiation of mouse macrophages has been well established. Mice that are deficient for either CSF-1 (Csf1$^{op/op}$) or its receptor (Csf1$^{-/-}$) exhibit severe reduction in macrophage and osteoclast frequencies, osteopetrosis, tooth eruption failure, developmental defects in various tissues, including nervous system, male and female fertility, the dermis and synovial membranes. While these studies have provided very important insights into the roles of CSF-1 in mice, the significance of CSF-1 in human hematopoiesis remains largely unknown. In this regard, the mice described herein will serve as a valuable tool, because it will enable improved understanding of the physiology and functions of cytokines in human hematopoiesis and hematopoietic cell function. Additionally, this mouse may be used to model disease and test the effects of agents on the human immune system. This mouse model is a valuable tools in understanding the pathophysiology and in the treatment of several human disorders and diseases.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

We claim:

1. A humanized M-CSF mouse, comprising:
   a Rag2 gene knock-out;
   an IL2rg gene knock-out;
   a nucleic acid sequence incorporated into the genome of the humanized M-CSF mouse, which sequence encodes a human M-CSF protein and is operably linked to the endogenous promoter of the mouse M-CSF gene at the mouse M-CSF locus;
   wherein the mouse expresses M-CSF RNA encoded by the nucleic acid sequence in bone marrow, spleen, blood, liver, brain, testis and kidney.

2. The humanized M-CSF mouse according to claim 1, wherein the mouse comprises two copies of the nucleic acid sequence.

3. The humanized M-CSF mouse according to claim 1, wherein the mouse comprises a null mutation in at least one mouse M-CSF allele.

4. The humanized M-CSF mouse according to claim 3, wherein the null mutation is a deletion of mouse M-CSF exons 2-9.

5. The humanized M-CSF mouse according to claim 1, wherein the mouse comprises human cells.

6. The humanized M-CSF mouse according to claim 5, wherein the human cells are hematopoietic cells.

7. The humanized M-CSF mouse according to claim 6, wherein the mouse comprises an infection by a human pathogen.

8. A mouse model of the human hematopoietic system, comprising:
   (a) a mouse which comprises:
      a Rag2 gene knock-out;
      an IL2rg gene knock-out;
      a nucleic acid sequence incorporated into the genome of the mouse, which sequence encodes a human M-CSF protein and is operably linked to the endogenous promoter of the mouse M-CSF gene at the mouse M-CSF locus; and
   (b) human hematopoietic cells, wherein the mouse expresses M-CSF RNA encoded by the nucleic acid sequence in bone marrow, spleen, blood, liver, brain, lung, testis and kidney.

9. The mouse model according to claim 8, wherein the mouse comprises a null deletion for at least one mouse M-CSF allele.

10. The mouse model according to claim 8, wherein the mouse exhibits one or more characteristics selected from:
   a. exhibits a frequency of hCD14$^+$CD33$^+$ cells of spleen that is 2- to 6-fold higher than hCD14$^+$CD33$^+$ in an engrafted mouse that does not express hM-CSF;
   b. exhibits a frequency in hCD14$^+$CD33$^+$ cells of peripheral blood that is 2- to 8-fold higher than hCD14$^+$CD33$^+$ in an engrafted mouse that does not express hM-CSF;
   c. exhibits a level of hCD14$^+$CD33$^+$ monocyte/macrophage lineage cells in blood of about 15 to about 40%;
   d. exhibits a level of hCD14$^+$CD33$^+$ monocyte/macrophage lineage cells in blood of about 5 to about 15% at about 20 weeks of age;
   e. exhibits a response to LPS injection that is about 1.5- to about 6-fold greater with respect to percentage of hCD14$^+$CD33$^+$ cells in liver than mice that lack a human M-CSF;
   f. exhibits an enhanced production of hCD14$^+$CD33$^+$ hCD45$^+$ cells in spleen about 48 hours following LPS injection, wherein the enhancement is about 2- to about 5-fold over an engrafted mouse that lacks hM-CSF;
   g. exhibits an enhanced production of serum human IL-6 in response to LPS, wherein the level of hIL-6 about 6 hours after LPS injection is enhanced about 2- to about 5-fold over an engrafted mouse that lacks a hM-CSF;
   h. exhibits in vitro secretion by a monocyte and/or macrophage upon LPS stimulation that is about 2- to 3-fold higher with respect to hTNFα than an engrafted mouse that lacks a hM-CSF gene;
   i. exhibits in vitro secretion by a monocyte and/or macrophage upon LPS stimulation that is about 2- to 4-fold higher with respect to hIL-6 than an engrafted mouse that lacks a hM-CSF gene;
   j. exhibits in vitro secretion by a monocyte and/or macrophage upon poly I:C stimulation that is about 3- to 6-fold higher with respect to hIFNα than an engrafted mouse that lacks a hM-CSF gene;
   k. exhibits in vitro secretion by a monocyte and/or macrophage upon poly I:C stimulation that is about 2- to 3-fold higher with respect to hIFNβ than an engrafted mouse that lacks a hM-CSF gene;
   l. exhibits enhanced phagocytosis as compared with a genetically modified and engrafted mouse that lacks a hM-CSF gene;
   m. exhibits enhanced chemotaxis in vitro in response to Mip3β as compared with a genetically modified engrafted mouse that lacks a hM-CSF gene; and
   n. exhibits upregulation in vitro of a co-stimulatory molecule in response to LPS stimulation, wherein the co-stimulatory molecule is selected from human CD40, human CD80, human CD86, human HLA-DR, and a combination thereof.

11. The mouse model according to claim 10, wherein the mouse exhibits two or more of said characteristics.

12. The mouse model according to claim 10, wherein the mouse exhibits three or more of said characteristics.

13. A mouse model of a human pathogen infection, comprising:
   (a) a mouse, wherein the mouse comprises
      a Rag2 gene knock-out;
      an IL2rg gene knock-out;

a nucleic acid sequence incorporated into the genome of the mouse, which sequence encodes a human M-CSF protein and is operably linked to the endogenous promoter of the mouse M-CSF gene at the mouse M-CSF locus;

(b) human hematopoietic cells; and (c) an infection by a human pathogen, wherein the mouse expresses M-CSF RNA encoded by the nucleic acid sequence in bone marrow, spleen, blood, liver, brain, lung, testis and kidney.

14. The mouse model according to claim 13, wherein the pathogen is selected from a virus, a fungus, and a bacterium.

15. The mouse model according to claim 14, wherein the bacterium is a mycobacterium or an enterobacterium.

16. The mouse model according to claim 9, wherein the null deletion is a deletion of mouse M-CSF exons 2-9.

* * * * *

UNITED STATES PATENT AND TRADEMARK OFFICE
CERTIFICATE OF CORRECTION

PATENT NO. : 8,847,004 B2  
APPLICATION NO. : 13/372787  
DATED : September 30, 2014  
INVENTOR(S) : Andrew J. Murphy et al.

Page 1 of 1

It is certified that error appears in the above-identified patent and that said Letters Patent is hereby corrected as shown below:

In the Claims

In claim 1, line 18, please insert the word --and-- after "knock-out;".

In claim 1, line 26, please insert the word --lung,-- after the word "brain," and before the word "testis".

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 1
tactgtagcc acatgattgg ga                                            22

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
cctgtgtcag tcaaaggaac                                               20

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
cgacatggct gggctccc                                                 18

<210> SEQ ID NO 4
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
cgcatggtct catctattat                                                    20

<210> SEQ ID NO 5
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 5
gtactgcaga atctctcctt tctcctg                                            27

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 6
gtgtctagat ctgacaacct cccaggcaca                                         30

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
ttgtgcttct ccactacagc                                                    20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
ctgtaagtct gttaatgaag                                                    20

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
aaggacctct cgaagtgttg gata                                               24

<210> SEQ ID NO 10
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 10
```

-continued catttaaaag gaactgttga caacg                                              25

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
cttcctcctc ctgaggagtc                                                    20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
cctgaccaag gaaagcaaag                                                    20

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 13
ccaggaatgt ccactatgga ttc                                                23

<210> SEQ ID NO 14
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 14
actgctcctt gaccctgctc tgactca                                            27

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
tgggctgact tcccaaagg                                                     19

<210> SEQ ID NO 16
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 16
ttaggtgcta gtaggctgga aagtg                                              25

<210> SEQ ID NO 17
<211> LENGTH: 30
<212> TYPE: DNA

```
<213> ORGANISM: Artificial Sequence
<220> FEATURE:
<223> OTHER INFORMATION: synthetic oligonucleotide

<400> SEQUENCE: 17
tgcaatcgca gcttctctcc ttactaggct                              30

<210> SEQ ID NO 18
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 18
aataggaaga acgaacaggt ctaatacc                                28

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
gctgcttgcc tgggttagtg                                         20

<210> SEQ ID NO 20
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 20
tgcccaggaa catcaaccac tgattctg                                28

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 21
gagggacagc agacctcaga ag                                      22

<210> SEQ ID NO 22
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 22
ggtggagagg ctattcggc                                          19

<210> SEQ ID NO 23
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 23
tgggcacaac agacaatcgg ctg                                     23
```

```
<210> SEQ ID NO 24
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 24
gaacacggcg gcatcag                                                    17
```